US012624377B2

(12) United States Patent
Lynch et al.

(10) Patent No.: US 12,624,377 B2
(45) Date of Patent: May 12, 2026

(54) SYSTEMS AND METHOD FOR THE PRODUCTION OF GRIFFITHSIN AND RELATED PROTEINS

(71) Applicant: Duke University, Durham, NC (US)

(72) Inventors: Michael Lynch, Durham, NC (US); John Decker, Durham, NC (US)

(73) Assignee: Duke University, Durham, NC (US)

( * ) Notice: Subject to any disclaimer, the term of this patent is extended or adjusted under 35 U.S.C. 154(b) by 853 days.

(21) Appl. No.: 17/906,501

(22) PCT Filed: Mar. 19, 2021

(86) PCT No.: PCT/US2021/023083

§ 371 (c)(1),
(2) Date: Sep. 16, 2022

(87) PCT Pub. No.: WO2021/188859

PCT Pub. Date: Sep. 23, 2021

(65) Prior Publication Data

US 2023/0257791 A1     Aug. 17, 2023

Related U.S. Application Data

(60) Provisional application No. 62/992,557, filed on Mar. 20, 2020.

(51) Int. Cl.
| | |
|---|---|
| *C07K 14/00* | (2006.01) |
| *A61K 8/64* | (2006.01) |
| *C07K 14/405* | (2006.01) |
| *C12N 15/63* | (2006.01) |
| *C12N 15/70* | (2006.01) |
| *C12P 21/02* | (2006.01) |

(52) U.S. Cl.
CPC ........... *C12P 21/02* (2013.01); *C07K 14/405* (2013.01); *C12N 15/635* (2013.01); *C12N 15/70* (2013.01); *C12N 2800/101* (2013.01); *C12N 2830/002* (2013.01)

(58) Field of Classification Search
CPC ........ C12N 2800/101; C12N 2830/002; C12N 15/70; C12P 21/02; C07K 14/405
See application file for complete search history.

(56) References Cited

PUBLICATIONS

International Search Report and Written Opinion issued in PCT application No. PCT/US21/23083, mailing date Sep. 15, 2021.
Giomarelli, B., et al., "Recombinant production of anti-HIV protein, griffithsin, by auto-induction in a fermentor culture", Protein Expression and Purification 47 (2006) 194-202.

(Continued)

*Primary Examiner* — Maryam Monshipouri
(74) *Attorney, Agent, or Firm* — BENESCH, FRIEDLANDER, COPLAN & ARONOFF LLP

(57) ABSTRACT

Methods and kits are provided for producing Griffithsin. The methods include providing a genetically modified microorganism comprising a gene encoding Griffithsin protein operably linked to an inducible promotor and growing the genetically modified microorganism under conditions that induce the promotor and cause expression of griffithisin. The Griffithsin is purified by releasing Griffithsin from the microorganism by cellular disruption, performing a precipitation step to remove contaminating protein and nucleic acids, and performing an anion exchange chromatography step.

10 Claims, 14 Drawing Sheets

Specification includes a Sequence Listing.

3. Supplementary Methods

| Supplemental Table 1: Plasmids and strain used in this study | | | | | |
|---|---|---|---|---|---|
| Plasmid | Insert | promoter | ori | Res | Source |
| pHC-Kan-phoAp-GRFT | GRFT | pho A p26 | col E1 | Kan | This Study |

| Strain used in this study | | |
|---|---|---|
| Strain | Genotype | Source |
| DLF_0025 | F-, λ-, Δ(araD-araB)567, 1acZ4787(del)(::miB-3) , 1ph-I, Δ(rhaD-rhaB)568, hsdR514, ΔackA-pta, ΔpoxB, ΔpflB, ΔldhA, ΔadhE, ΔiclR, ΔarcA, ΔsspB::frt, Δcas3::ugpBp-sspB-J231 00p-casA | 27 |

Ori-origin of replication., Res - resistance marker, Kan - kanamycin

(56)         References Cited

PUBLICATIONS

Oh, L., "Evaluation of a Low Cost, Downstream Purification Process for Griffithsin—a Potential Broad Spectrum Viral Entry Inhibitor Produced in Engineered E. col" 1-30 .. Dissertation. 2017; Entire Document.

Wingfield, P., "Protein precipitation using ammonium sulfate", Current protocols in protein science, Appendix 3, Appendix-3F, https://doi.org/10.1002/04 71140864.psa03fs13, 2001.

Luo, M. et al., "A general platform for efficient extracellular expression and purification of Fab from *Escherichia coli*. Appl Microbiol Biotechnol", Apr. 2019; 103(8):3341-3353. doi: 10.1007/s00253-019-09745-8. Epub Mar. 18, 2019.

Kante, R. K. et al., "Efficient and Easily Scalable Protein Folding Strong Anion Exchange Chromatography for Renaturation and Simultaneous Purification of Recombinant Human Asparaginase from *E. coli*", Biotechnol. Prag., 2018, vol. 34, No. 4.

Vamvaka, E., et al. "Rice endosperm is cost-effective for the production of recombinant griffithsin with potent activity against HIV", Plant Biotechnology Journal (2016) 14, pp. 1427-1437.

Alam, A., et al. (2018), "Technoeconomic modeling of plant-based griffithsin manufacturing", Front. Bioeng. Biotechnol. 6:102. doi: 10.3389/fbioe.2018. 00102.

Albasarah, Y. Y., et al., (2010), "Stabilizing protein formulations during air-jet nebulization", Int. J. Pharm. 402, 140-145. doi: 10.1016/j.ijpharm.2010.09.042.

Bagdonaite, I., et al., (2018), "Global aspects of viral glycosylation", Glycobiology 28, 443-467. doi: 10.1093/glycob/cwy021.

Barton, C., et al. (2014), "Activity of and effect of subcutaneous treatment with the broad-Spectrum antiviral lectin griffithsin in two laboratory rodent models", Antimicrob. Agents Chemother. 58, 120-127. doi: 10.1128/aac.014 07-13.

Blackstone, E. A., et al., (2007), "Biopharmaceuticals: the economic equation", Biotechnol. Healthc. 4, 41-45.

Burg, J. M., et al., (2016), "Large-scale bioprocess competitiveness: the potential of dynamic metabolic control in two-stage fermentations", Curr. Opin. Chem. Eng. 14, 121-136. doi: 10.1016/j.coche. 2016.09.008.

Center for Drug Evaluation and Research, (2019). Pyrogen and Endotoxins Testing: Questions and Answers. U.S. Food and Drug Administration. Available at: https://www.fda.gov/regulatory-information/search-fda-guidancedocuments/pyrogen-and-endotoxins-testing-questions-and-answers (accessed Mar. 21, 2020).

Derby, N., et al. (2018), "Griffithsin carrageenan fast dissolving inserts prevent SHIV HSV-2 and HPV infections in vivo", Nat. Commun. 9:3881.

Ewen, M., et al., (2019), "Insulin prices, availability and affordability in 13 low-income and middle-income countries", BMJ Glob. Health 4, e001410. doi: 10.1136/bmjgh-2019-001410.

Farid, S. S. (2017). "Process economic drivers in industrial monoclonal antibody manufacture," in Process Scale Purification of Antibodies, ed. U. Gottschalk, (Hoboken, NJ: John Wiley & Sons, Inc), 445-466. doi: 10.1002/9781119126942. ch21.

Fuqua, J. L., et al., (2015a), "Bulk production of the antiviral lectin griffithsin", Plant Biotechnol. J. 13, 1160-1168.

Fuqua, J. L., et al., (2015b), "Improving the large scale purification of the HIV microbicide, griffithsin", BMC Biotechnol. 15:12. doi: 10.1186/s12896-015-0120-5.

Giomarelli, B., et al. (2006), "Recombinant production of anti-HIV protein, griffithsin, by auto-induction in a fermentor culture", Protein Expr. Purif. 47, 194-202. doi: 10.1016/j.pep.2005.10.014.

Gotham, D., et al., (2018), "Production costs and potential prices for biosimilars of human insulin and insulin analogues", BMJ Glob. Health 3:e000850. doi: 10.1136/bmjgh-2018-000850.

Günaydin, G., et al. (2019), "Impact of Q-Griffithsin anti-HIV microbicide gel in nonhuman primates: in situ analyses of epithelial and immune cell markers in rectal mucosa", Sci. Rep. 9:18120.

Hassouneh, W., et al.. (2010), "Elastin-like polypeptides as a purification tag for recombinant proteins" Curr. Protoc. Protein Sci. Chapter 6: Unit 6.11.

Huang, L.-K., et al., (1995), "Image thresholding by minimizing the measures of fuzziness", Pattern Recogn. 28, 41-51. doi: 10.1016/0031-3203(94) e0043-k.

Hubbuch, J., et al., (2019), "Preparative Protein Crystallization", Chem. Eng. Technol. 42, 2275-2281. doi: 10.1002/ceat.201800627.

Ishag, H. Z. A., et al. (2013), "Griffithsin inhibits Japanese encephalitis virus infection in vitro and in vivo", Arch. Virol. 158, 349-358. doi: 10.1007/s00705-012-1489-2.

Jones, B., et al., (2013), "Definitive screening designs with added two-level categorical factors", J. Commod. Sci. Technol. Qual. 45, 121-129. doi: 10.1080/00224065.2013.11917921.

Kelley, B. (2007), "Very large scale monoclonal antibody purification: the case for conventional unit operations", Biotechnol. Prog. 23, 995-1008. doi: 10.1021/ bp070117s.

Kelley, B. (2009), "Industrialization of mAb production technology: the bioprocessing industry at a crossroads", MAbs 1, 443-452. doi: 10.4161/mabs.1.5.9448.

Kouokam, J. C., et al., (2016), "Studies in a murine model confirm the safety of griffithsin and advocate its further development as a microbicide targeting HIV-1 and other enveloped viruses", Viruses 8:311. doi: 10.3390/v8110311.

Li, G., et al., (2020), "Therapeutic options for the 2019 novel coronavirus (2019-nCoV)", Nat. Rev. Drug Discov. 19, 149-150. doi: 10.1038/d41573-020-00016-0.

Li, S., et al., (2020), "Dynamic control over feedback regulation improves stationary phase fluxes in engineered *E. coli*" bioRxiv [Preprint] doi: 10.1101/2020.07.26.219949.

Martinez, M., et al., (2019), "Precipitation as an enabling technology for the intensification of biopharmaceutical manufacture", Trends Biotechnol. 37, 237-241. doi: 10.1016/j.tibtech.2018. 09.001.

Menacho-Melgar, et al., (2020a), "Improved two-stage protein expression and purification via autoinduction of both autolysis and auto DNA/RNA hydrolysis conferred by phage lysozyme and DNA/RNA endonuclease", Biotechnol. Bioeng. 1-9.

Menacho-Melgar, R. et al. (2020b), Scalable, two-stage, autoinduction of recombinant protein expression in *E. coli* utilizing phosphate depletion:, Biotechnol. Bioeng. 26:44.

Meuleman, P., et al. (2011), "Griffithsin has antiviral activity against hepatitis C virus", Antimicrob. Agents Chemother. 55, 5159-5167. doi: 10.1128/aac.006 33-11.

Moreb, E. A., et al., (2020), "Media Robustness and scalability of phosphate regulated promoters useful for two-stage autoinduction in *E. coli*", ACS Synthet. Biol. 9, 1483-1486. doi: 10.1021/acssynbio. 0c00182.

Mori, T., et al. (2005), "Isolation and characterization of griffithsin, a novel HIV-inactivating protein, from the red alga *Griffithsia sp*," J. Biol. Chem. 280, 9345-9353. doi: 10.1074/jbc.m411122200.

Moulaei, T., et al. (2010), "Monomerization of viral entry inhibitor griffithsin elucidates the relationship between multivalent binding to carbohydrates and anti-HIV activity", Structure 18, 1104-1115. doi: 10.1016/j.str.2010.05.016.

Nair, A. B., et al., (2016), "A simple practice guide for dose conversion between animals and human", J. Basic Clin. Physiol. Pharmacol. 7, 27-31.

Nixon, B., et al. (2013), "Griffithsin protects mice from genital herpes by preventing cell-to-cell spread", J. Virol. 87, 6257-6269. doi: 10.1128/jvi.00012-13.

O'Keefe, B. R., et al. (2010). "Broad-spectrum in vitro activity and in vivo efficacy of the antiviral protein griffithsin against emerging viruses of the family Coronaviridae", J. Virol. 84, 2511-2521. doi: 10.1128/jvi.02322-09.

O'Keefe, B. R., et al. (2009), "Scaleable manufacture of HIV-1 entry inhibitor griffithsin and validation of its safety and efficacy as a topical microbicide component", Proc. Natl. Acad. Sci. U.S.A. 106, 6099-6104. doi: 10.1073/pnas.0901506106.

Petrides, D., et al., (2014), "Biopharmaceutical Process Optimization with Simulation and Scheduling Tools", Bioengineering 1, 154-187. doi: 10.3390/bioengineering1040154.

(56)                    References Cited

PUBLICATIONS

Rueden, C. T., et al. (2017), "ImageJ2: imageJ for the next genera-tion of scientific image data", BMC Bioinformatics 18:529. doi: 10.1186/s12859-017-1934-z.

Saqib, A., et al., (2018), "Availability and affordability of biologic versus non-biologic anticancer medicines: a cross-sectional study in Punjab. Pakistan", BMJ Open 8:e019015. doi: 10.1136/bmjopen-2017-019015.

Sato, Y., et al., (2011), "High mannose-specific lectin (KAA-2) from the red alga *Kappaphycus alvarezii* potently Inhibits influenza virus infection in a strain-independent manner", Biochem. Biophys. Res. Commun. 405, 291-296. doi: 10.1016/j.bbrc.2011.01.031.

Schindelin, J., et al. (2012), "Fiji: an open-source platform for biological-image analysis", Nat. Methods 9, 676-682. doi: 10.1038/nmeth.2019.

Steckel, H., et al., (2003), "Effect of excipients on the stability and aerosol performance of nebulized aviscumine", J. Aerosol. Med. 16, 417-432. doi: 10.1089/089426803772455677.

Straathof, A. J. J. (2011), "The Proportion of Downstream Costs in Fermentative Production Processes", Study to Evaluate the Safety of Griffithsin in a Carrageenan Gel in Healthy Women US National Library of Medicine Clinical Trials Database. Available at: https://clinicaltrials. gov/ct2/show/NCT02875119 (Accessed Feb. 2, 2020).

The United States Pharmacopeial Convention, (2011). Bacterial Endotoxins Monograph. Rockville, MD: The United States Pharmacopeial Convention.

Toumi, A., e al., (2010), "Design and optimization of a large scale biopharmaceutical facility using process simulation and scheduling tools", Pharm. Eng. 30, 1-9.

US National Library of Medicine, (2020), "Griffithsin-based Rectal Microbicide for PREvention of Viral ENTry (Prevent)", Clinical Trials Database. Available at: https://clinicaltrials.gov/ct2/show/NCT04032717 (accessed Feb. 2, 2020).

Van Der Meer, F.J.U.M., et al. (2007), "Antiviral activity of carbohydrate-binding agents against Nidovirales in cell culture", Antiviral Res. 76, 21-29. doi: 10.1016/j.antiviral.2007.04.003.

Vigerust, D. J., et al., (2007), "Virus glycosylation: role in virulence and immune interactions", Trends Microbiol. 15, 211-218. doi: 10.1016/j.tim. 2007.03.003.

Walls, A. C., et al., (2020), "Structure, Function, and Antigenicity of the SARS-CoV-2 Spike Glycoprotein", Cell 181, 281-292.e6. doi: 10.1016/j.cell.2020.02.058.

Wang, X., et al., (2009), "Host cell proteins in biologics develop-ment: Identification, quantitation and risk assessment", Biotechnol. Bioeng. 103, 446-458. doi: 10.1002/bit.22304.

World Health Organization, (1998). Requirements for the use of animal cells as in vitro substrates for the Production of Biologicals (requirements for biological substances No. 50). in: WHO Expert Committee on Biological Standardization. Forty-seventh report. Geneva: World Health Organization.

Xue, J., et al., (2013), "The griffithsin dimer is required for high-potency inhibition of HIV-1: evidence for manipulation of the structure of gp120 as part of the griffithsin dimer mechanism", Antimicrob. Agents Chemother. 57, 3976-3989. doi: 10.1128/aac. 00332-13.

Decker et al., "Phase separationmethods for protein purification: A meta-analysis of purification performance and cost-effectiveness", Biotechnology Journal, 19(4), Apr. 2024.

3. Supplementary Methods

| Supplemental Table 1: Plasmids and strain used in this study | | | | | | |
|---|---|---|---|---|---|---|
| Plasmid | Insert | promoter | ori | Res | Source |
| pHC-Kan-phoAp-GRFT | GRFT | pho A p26 | col E1 | Kan | This Study |
| Strain used in this study | | | | | | |
| Strain | Genotype | | | | | Source |
| DLF_0025 | F-, λ-, Δ(araD-araB)567,1acZ4787(del)(::mlB-3) , 1ph-I, Δ(rhaD-rhaB)568, hsdR514, ΔackA-pta, ΔpoxB, ΔpflB, ΔldhA, ΔadhE, ΔiclR, ΔarcA, ΔsspB::frt, Δcas3::ugpBp-sspB-J231 00p-casA | | | | | 27 |
| Ori-origin of replication., Res - resistance marker, Kan - kanamycin | | | | | | |

FIG. 1

SYSTEMS AND METHOD FOR THE PRODUCTION OF GRIFFITHSIN AND RELATED PROTEINS

CROSS-REFERENCE TO RELATED APPLICATIONS

This application claims priority to U.S. Provisional Patent Application No. 62/992,557 filed Mar. 20, 2020, which is incorporated by reference herein in its entirety.

STATEMENT AS TO FEDERALLY SPONSORED RESEARCH

This invention was made with Government support under Federal Grant no. 12043956 awarded by the Office of Naval Research, Federal Grant no. EE0007563 awarded by the Department of Energy (DOE), R61 AI140485-01 awarded by the National Institute of Health (NIH/NIAID/DMID), and Federal Grant no. T32GM008555 awarded by the National institute of General Medical Sciences. The Federal Government has certain rights to this invention.

SEQUENCE LISTING

The instant application contains a Sequence Listing which has been filed electronically in ASCII format as 47381-47_ST25 created Mar. 19, 2021 that is 3,505 bytes in size and is hereby incorporated by reference in its entirety.

BACKGROUND

Griffithsin, a lectin, has potential to prevent and treat and prevent numerous viruses including HIV, HCV, HSV, SARS-CoV, and SARS-CoV-2. For SARS-CoV-2 prevention and treatment in the current pandemic, annual demand could reach billions of doses and affordability is paramount.

SUMMARY

The Summary is provided to introduce a selection of concepts that are further described below in the Detailed Description. This Summary is not intended to identify key or essential features of the claimed subject matter, nor is it intended to be used as an aid in limiting the scope of the claimed subject matter.

The present disclosure is based, in part, on lab-scale validation of a bioprocess that supports production volumes>20 tons per year (5 billion doses) at costs below $10,000/kg of Griffithsin ($0.04/dose) in a finished antiviral product. Recombinant expression in engineered *E. coli* enables Griffithsin titers>2.7 g/L. A single precipitation step removing >99% of host cell proteins and virtually all nucleic acids is followed by a single chromatography step removing residual endotoxin leading to pure, active Griffithsin. These results support the potential of biologics in very large scale, low-cost applications such as preventive antivirals against SARS-CoV-2 and highlight the importance of bioprocess innovations in enabling these applications.

Accordingly, one aspect of the present disclosure provides a process for the production and purification of Griffithsin or a related protein comprising, consisting of, or consisting essentially of: i) expressing the Griffithsin or the related protein in *E. coli* under the control of a low phosphate inducible promoter; ii) releasing the Griffithsin or the related protein expressed in (i) from the cell via cellular disruption or lysis; iii) performing a precipitation step to remove contaminating protein and nucleic acids performed at temperatures greater than 55 degrees Celsius, $(NH_4)_2SO_4$ concentrations greater than 0.8M and a pH less than 4; and vi) performing at least one anion exchange chromatography purification step.

In one aspect, the related protein has greater than 60% identity to Griffithsin or consists of multiple domains each having greater than 60% identity to Griffithsin.

In another aspect, the temperature during precipitation is greater than 55 degrees Celsius and less than 73 degrees Celsius.

In another aspect, the duration of heating to effect precipitation is between 5 and 60 minutes.

In another aspect, the concentration of $(NH_4)_2SO_4$ during precipitation is greater than 0.8 M and less than 1.4 M.

In other aspects, the pH during precipitation is greater than 2.5 and less than 4.

In another aspect, the concentration of $(NH_4)_2SO_4$ during anion exchange chromatography is greater than 30 mM and less than 60 mM.

In another aspect, the precipitates are removed by centrifugation. In yet another aspect, spray drying is used for the final formulation.

Other methods, features and/or advantages is, or will become, apparent upon examination of the following figures and detailed description. It is intended that all such additional methods, features, and advantages be included within this description and are protected by the accompanying claims.

BRIEF DESCRIPTION OF DRAWINGS

The novel features of the invention are set forth with particularity in the claims. A better understanding of the features and advantages of the present invention will be obtained by reference to the following detailed description that sets forth illustrative aspects, in which the principles of the invention are used, and the accompanying drawings of which:

FIG. 1 is a table summarizing plasmids and microorganism strains used in this study.

DETAILED DESCRIPTION

Figure 2:
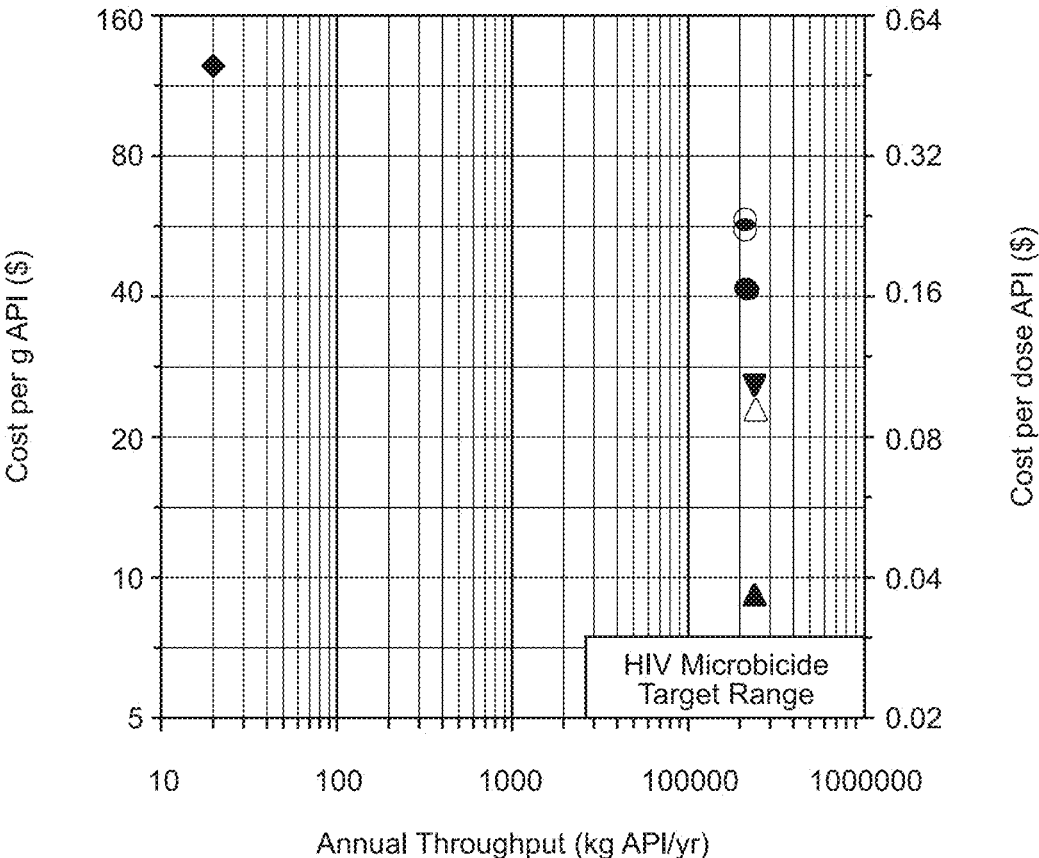
FIG. 2 is a graph showing the cost and scale for various GRFT manufacturing processes.

For the purposes of promoting an understanding of the principles of the present disclosure, reference will now be made to preferred aspects and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

I. Definitions

Unless otherwise defined, all technical and scientific terms used herein have the same meaning as commonly understood by one of ordinary skill in the art to which this invention pertains. In case of conflict, the present specification, including definitions, will control.

Unless otherwise specified, "a," "an," "the," "one or more of," and "at least one" are used interchangeably. The singular forms "a", "an," and "the" are inclusive of their plural forms.

The recitations of numerical ranges by endpoints include all numbers subsumed within that range (e.g., 0.5 to 5 includes 1, 1.5, 2, 2.75, 3, 3.80, 4, 5, etc.).

The term "about," when referring to a value or to an amount of mass, weight, time, volume, concentration, or percentage is meant to encompass variations of ±1% from the specified amount. The terms "comprising" and "including" are intended to be equivalent and open-ended. The phrase "consisting essentially of" means that the composition or method may include additional ingredients and/or steps, but only if the additional ingredients and/or steps do not materially alter the basic and novel characteristics of the claimed composition or method. The phrase "selected from the group consisting of" is meant to include mixtures of the listed group.

Moreover, the present disclosure also contemplates that in some aspects, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

The term "heterologous DNA," "heterologous nucleic acid sequence," and the like as used herein refers to a nucleic acid sequence wherein at least one of the following is true: (a) the sequence of nucleic acids is foreign to (i.e., not naturally found in) a given host microorganism; (b) the sequence may be naturally found in a given host microorganism, but in an unnatural (e.g., greater than expected) amount; or (c) the sequence of nucleic acids comprises two or more subsequences that are not found in the same relationship to each other in nature. For example, regarding instance (c), a heterologous nucleic acid sequence that is recombinantly produced will have two or more sequences from unrelated genes arranged to make a new functional nucleic acid, such as a nonnative promoter driving gene expression. The term "heterologous" is intended to include the term "exogenous" as the latter term is generally used in the art. With reference to the host microorganism's genome prior to the introduction of a heterologous nucleic acid sequence, the nucleic acid sequence that codes for the enzyme is heterologous (whether or not the heterologous nucleic acid sequence is introduced into that genome). As used herein, chromosomal and native and endogenous refer to genetic material of the host microorganism.

As used herein, the term "gene disruption," or grammatical equivalents thereof (and including "to disrupt enzymatic function," "disruption of enzymatic function," and the like), is intended to mean a genetic modification to a microorganism that renders the encoded gene product as having a reduced polypeptide activity compared with polypeptide activity in or from a microorganism cell not so modified. The genetic modification can be, for example, deletion of the entire gene, deletion or other modification of a regulatory sequence required for transcription or translation, deletion of a portion of the gene which results in a truncated gene product (e.g., enzyme) or by any of various mutation strategies that reduces activity (including to no detectable activity level) the encoded gene product. A disruption may broadly include a deletion of all or part of the nucleic acid sequence encoding the enzyme, and also includes, but is not limited to other types of genetic modifications, e.g., introduction of stop codons, frame shift mutations, introduction or removal of portions of the gene, and introduction of a degradation signal, those genetic modifications affecting mRNA transcription levels and/or stability, and altering the promoter or repressor upstream of the gene encoding the enzyme.

Bio-production, Micro-fermentation (microfermentation) or Fermentation, as used herein, may be aerobic, microaerobic, or anaerobic.

When the genetic modification of a gene product, i.e., an enzyme, is referred to herein, including the claims, it is understood that the genetic modification is of a nucleic acid sequence, such as or including the gene, that normally encodes the stated gene product, i.e., the enzyme.

Species and other phylogenic identifications are according to the classification known to a person skilled in the art of microbiology.

Enzymes are listed here within, with reference to a UniProt identification number, which would be well known to one skilled in the art. The UniProt database can be accessed online. When the genetic modification of a gene product, i.e., an enzyme, is referred to herein, including the claims, it is understood that the genetic modification is of a nucleic acid sequence, such as or including the gene, that normally encodes the stated gene product, i.e., the enzyme.

Where methods and steps described herein indicate certain events occurring in certain order, those of ordinary skill in the art will recognize that the ordering of certain steps may be modified and that such modifications are in accordance with the variations of the invention. Additionally, certain steps may be performed concurrently in a parallel process when possible, as well as performed sequentially.

The meaning of abbreviations is as follows: Unless otherwise specified GRFT refers to any Griffithsin variant. TFF refers to tangential flow filtration. BDS refers to bulk drug substance. HCP refers to host cell proteins. LPS refers to lipopolysaccharide. BV refers to bed volume. DSP refers to downstream recovery and purification. DoE refers to Design of Experiments. DEF refers to dead end filtration. CIP refers to clean in place (CIP). SIP refers to steam in place. EU refers to effective unit. FDI refers to fast-dissolve insert. WFI refers to water for injection. "C" means Celsius or degrees Celsius, as is clear from its usage, DCW means dry cell weight, "s" means second(s), "min" means minute(s), "h," "hr," or "hrs" means hour(s), "psi" means pounds per square inch, "nm" means nanometers, "d" means day(s), "µL" or "uL" or "ul" means microliter(s), "mL" means milliliter(s), "L" means liter(s), "mm" means millimeter(s), "nm" means nanometers, "mM" means millimolar, "µM" or "uM" means micromolar, "M" means molar, "mmol" means millimole(s), "p mol" or "uMol" means micromole(s)", "g" means gram(s), "µg" or "ug" means microgram(s) and "ng" means nanogram(s), "PCR" means polymerase chain reaction, "OD" means optical density, "OD600" means the optical density measured at a photon wavelength of 600 nm, "kDa" means kilodaltons, "g" means the gravitation constant, "bp" means base pair(s), "kbp" means kilobase pair(s), "% w/v" means weight/volume percent, "% v/v" means volume/volume percent, "aTc" means anhydrotetracycline, "rpm" means revolutions per minute, "HPLC" means high performance liquid chromatography, and "GC" means gas chromatography.

Griffithsin refers to any protein that is a small lectin comparable to that originally isolated from red algae Griffithsia. The GRFT binds and neutralizes many enveloped viruses. GRFT has a selectivity for high-mannose glycans. An exemplary GRFT sequence has been reported by Mori et al. An oxidation-stable variant Q-GRFT has been reported by Günaydin et al. In some aspects of the invention, a codon optimized synthetic DNA based on the reported GRFT sequences is the source of the GRFT protein to be produced and purified. Though it is appreciated that the methods described herein are widely applicable to any GRFT sequence or sequence variant.

Overview of Invention Aspects

One aspect. The present disclosure is based, in part, on lab-scale validation of a bioprocess that supports production volumes>20 tons per year (5 billion doses) at costs below $10,000/kg of Griffithsin ($0.04/dose) in a finished antiviral product. Recombinant expression in engineered *E. coli* enables Griffithsin titers>2.7 g/L. A single precipitation step removing >99% of host cell proteins and virtually all nucleic acids is followed by a single chromatography step removing residual endotoxin leading to pure, active Griffithsin. These results support the potential of biologics in very large scale, low-cost applications such as preventive antivirals against SARS-CoV-2 and highlight the importance of bioprocess innovations in enabling these applications.

Accordingly, one aspect of the present disclosure provides a process for the production and purification of Griffithsin or a related protein comprising, consisting of, or consisting essentially of: i) expressing the Griffithsin or the related protein in *E. coli* under the control of a low phosphate inducible promoter; ii) releasing the Griffithsin or the related protein expressed in (i) from the cell via cellular disruption or lysis; iii) performing a precipitation step to remove contaminating protein and nucleic acids performed at temperatures greater than 55 Celsius, $(NH_4)_2SO_4$ concentrations greater than 0.8M and a pH less than 4; and vi) performing at least one anion exchange chromatography purification step.

In one aspect, the related protein has greater than 60% identity to Griffithsin or consists of multiple domains each having greater than 60% identity to Griffithsin.

In another aspect, the temperature during precipitation is greater than 55 degrees Celsius and less than 73 degrees Celsius.

In another aspect, the duration of heating to effect precipitation is between 5 and 60 minutes.

In another aspect, the concentration of $(NH_4)_2SO_4$ during precipitation is greater than 0.8 M and less than 1.4 M.

In other aspects, the pH during precipitation is greater than 2.5 and less than 4.

In another aspect, the concentration of $(NH_4)_2SO_4$ during anion exchange chromatography is greater than 30 mM and less than 60 mM.

In another aspect, the precipitates are removed by centrifugation.

In yet another aspect, spray drying is used for the final formulation.

Disclosed Aspects are Non-Limiting

While various aspects of the present invention have been shown and described herein, it is emphasized that such aspects are provided by way of example only. Numerous variations, changes and substitutions may be made without departing from the invention herein in its various aspects. Specifically, and for whatever reason, for any grouping of compounds, nucleic acid sequences, polypeptides including specific proteins including functional enzymes, metabolic pathway enzymes or intermediates, elements, or other compositions, or concentrations stated or otherwise presented herein in a list, table, or other grouping unless clearly stated otherwise, it is intended that each such grouping provides the basis for and serves to identify various subset aspects, the subset aspects in their broadest scope comprising every subset of such grouping by exclusion of one or more members (or subsets) of the respective stated grouping. Moreover, when any range is described herein, unless clearly stated otherwise, that range includes all values therein and all sub-ranges therein.

Also, and more generally, in accordance with disclosures, discussions, examples and aspects herein, there may be employed conventional molecular biology, cellular biology, microbiology, and recombinant DNA techniques within the skill of the art. Such techniques are explained fully in the literature. See, e.g., Sambrook and Russell, "Molecular Cloning: A Laboratory Manual," Third Edition 2001 (volumes 1-3), Cold Spring Harbor Laboratory Press, Cold Spring Harbor, N.Y.; Animal Cell Culture, R. I. Freshney, ed., 1986. These published resources are incorporated by reference herein.

The following published resources are incorporated by reference herein for description useful in conjunction with the invention described herein, for example, methods of industrial bio-production of chemical product(s) from sugar sources, and also industrial systems that may be used to achieve such conversion (Biochemical Engineering Fundamentals, $2^{nd}$ Ed. J. E. Bailey and D. F. Ollis, McGraw Hill, New York, 1986, e.g. Chapter 9, pages 533-657 for biological reactor design; Unit Operations of Chemical Engineering, $5^{th}$ Ed., W. L. McCabe et al., McGraw Hill, New York 1993, e.g., for process and separation technologies analyses; Equilibrium Staged Separations, P. C. Wankat, Prentice Hall, Englewood Cliffs, NJ USA, 1988, e.g., for separation technologies teachings).

All publications, patents, and patent applications mentioned in this specification are entirely incorporated by reference.

EXAMPLES

For the purposes of promoting an understanding of the principles of the present disclosure, reference will now be made to preferred aspects and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Cost-Effective Large Volume Production of the Anti-Viral Lectin Griffithsin, a SARS-CoV-2 Therapy and Prophylactic Materials & Methods Microorganisms Features as described and claimed herein may be provided in a microorganism selected from the listing herein, or another suitable microorganism, that also comprises one or more natural, introduced, or enhanced product bio-production pathways. Thus, in some aspects the microorganism(s) comprise an endogenous product production pathway (which may, in some such aspects, be enhanced), whereas in other aspects the microorganism does not comprise an endogenous product production pathway.

More particularly, based on the various criteria described herein, suitable microbial hosts for the bio-production of a chemical product generally may include, but are not limited to the organisms described herein.

The host microorganism or the source microorganism for any gene or protein described here may be selected from the following list of microorganisms: *Citrobacter, Enterobacter, Clostridium, Klebsiella, Aerobacter, Lactobacillus, Aspergillus, Saccharomyces, Schizosaccharomyces, Zygosaccharomyces, Pichia, Kluyveromyces, Candida, Hansenula, Debaryomyces, Mucor, Torulopsis, Methylobacter, Escherichia, Salmonella, Bacillus, Streptomyces*, and *Pseudomonas*. In some aspects the host microorganism is an *E. coli* microorganism.

Reagents & Media

Unless otherwise stated all reagents and materials were of the highest grade possible from Sigma Aldrich. Kanamycin sulfate at a working concentration of 35 mg/L was used for selection.

Strains and Plasmids

Referring to FIG. 1, *E. coli* strain DLF 0025 was constructed as previously reported. The GRFT sequence as reported by Mori et al was codon-optimized and incorporated in a synthetic DNA construct (IDT, Coralville, IA) under the control of a low phosphate inducible phoA promoter. This gene was then inserted into the pSMART-HC-Kan vector (Lucigen, Middleton, WI) using 2× Hifi DNA Assembly Master Mix from New England Biolabs (Ipswich, MA) according to manufacturer's instructions. The resulting plasmid was pHC-Kan-phoAp-GRFT.

Fermentation

Microfermentations using Autoinduction Broth as well as instrumented fermentations were performed as previously reported by Menacho-Melgar et al.

Technoeconomic Analysis and in Silico Bioprocess Modeling

Models of GRFT production bioprocesses were created in SuperPro Designer (Intelligen, Inc, Scotch Plains, NJ).

Design of Experiments and Precipitation Optimization

Design of experiments (DoE) was used to facilitate the screening of precipitation conditions for GRFT purification. This was accomplished in two rounds of experiments. In the first screening round, a Definitive Screening Design (JMP®, Version 14. SAS Institute, Cary, NC) was used with two outcomes, GRFT separation factor and yield, and four factors: incubation temperature and time, pH, and ammonium sulfate concentration. In a second round guided by the results of the first, a central composite design was used with the addition of protein concentration as a factor and the removal of time and ammonium sulfate concentration as factors. Predictive models were constructed using standard least-squares linear regression.

DLF_Z0025 containing pSMART-phoA-GRFT was cultured in shake flasks as previously described. Cells were then harvested by centrifugation and pellets were stored at −60° C. until lysis. Cell pellets were resuspended in 50 mM phosphate buffer at pH 7.2 to a density of approximately 300-400 $OD_{600}$ and supplemented with Halt protease inhibitor (Thermo Fisher Scientific, Waltham, MA) at 1× concentration. Cells were lysed at 4° C. using a sonicator with 2 mM probe operated at 45% power for 48 cycles of 15 seconds on followed by 45 seconds off. Lysate was cleared by centrifugation at 4° C., and total protein concentration was measured using the Pierce™ Coomassie Plus Bradford Assay Kit (Thermo Fisher Scientific, Waltham, MA) and normalized to twice the desired protein concentration for each precipitation condition to be tested. A lysate standard for yield quantification was also prepared by dilution to 0.25 g/L in lysis buffer, 1:1 addition of 2× Laemmli sample buffer (Bio-Rad Laboratories, Hercules, CA), heating at 95° C. for 5 min, and subsequent storage at −20° C.

Precipitation buffers were prepared in 200 μL PCR tubes by combining ultrapure water, saturated ammonium sulfate solution, and concentrated HCl or NaOH to achieve the desired pH and degree of ammonium sulfate saturation in 100 μL. Clarified lysate was added to each buffer at a 1:1 volume ratio to achieve the desired protein concentration in 200 μL, and samples were incubated in thermocyclers or dry heat blocks for the times and temperatures prescribed by each DOE condition. Immediately after each incubation period, samples were harvested and clarified by centrifugation. Because the yield of GRFT in each supernatant was uncertain until SDS-PAGE analysis, supernatants were diluted in lysis buffer such that a hypothetical 50% yield of GRFT would result in equal GRFT concentrations between a given sample and the lysate standard (e.g., samples with initial concentrations of 5 g/L total protein were diluted 10×; 2.5 g/L by 5×; etc.). Diluted supernatants were then denatured in Laemmli buffer and stored at −20° C.

Separation factors and yields for GRFT from each precipitation condition were analyzed by densitometry of SDS-PAGE gels. 15-well NuPAGE Bis-Tris gels (Thermo Fisher Scientific, Waltham, MA) were loaded with 10 μL per well of each sample (including 5 μL Laemmli buffer) and run in MOPS buffer at 200 V. Each gel included a lysate standard prepared as previously described from the same batch of lysate as the purified samples on that gel, to allow yield calculations. Gels were stained with SYPRO™ Ruby Protein Gel Stain (Thermo Fisher Scientific, Waltham, MA) according to manufacturer instructions and imaged. Densitometry was conducted using FIJI2, 8 29. Standard rolling ball background subtraction was applied with a ball radius of 400 pixels (>2× the largest dimension of any band), and bands were automatically identified and integrated using FIJI's built-in thresholding tool based on the method of Huang and Wang.30 Separation factors were calculated as the ratio of GRFT to contaminants in a sample divided by the corresponding ratio in the lysate standard. Yield was calculated as the dilution-corrected ratio between the GRFT signal in a purified sample and that in the lysate standard. The amount of GRFT in each sample and standard was within the linear range of the stain (data not shown).

Anion Exchange FPLC for Endotoxin Removal

Supernatants from the optimal precipitation step described above were pooled, exchanged by diafiltration into 100 mM pH 2.73 citrate buffer containing 50 mM ammonium sulfate (sample buffer) and stored briefly at 4° C. Strong anion exchange FPLC was performed in flow-through mode using a 5 mL HiTrap® Q FF column on an AKTA Pure instrument (GE Healthcare Life Sciences, Marlborough, MA). The flow path and column were equilibrated with 8 column volumes of sample buffer, followed by manual washing and equilibration of the 500 µL sample loop, injection of 1000 µL of sample at a flow rate of 10 mL/min, and a further wash with sample buffer at a flow rate of 10 mL/min. A single peak was observed to flow through immediately and was collected for analysis.

Griffithsin Purity and Activity Assays

Endotoxin was quantified using the Pierce™ Chromogenic Endotoxin Quant Kit (Thelmo Fisher Scientific, Waltham, MA) according to manufacturer instructions. DNA contaminants were assessed by agarose gel electrophoresis with ethidium bromide staining. The activity of precipitation-purified GRFT was assayed by measuring its binding to gp140 using a Biacore T200 surface plasmon resonance instrument with a CMS sensor chip (GE Healthcare Life Sciences, Marlborough, MA). Recombinant gp140 from the clade C strain 92BR025 was obtained from Sino Biological, Inc. (Beijing, China) and immobilized to approximately 300 response units via standard NHS-EDC covalent coupling. The immobilized surface was quenched with ethanolamine and equilibrated with PBS at 50 µL/min for several hours. GRFT was prepared in triplicate dilution series at concentrations of 400, 200, 100, 50, and 12.5 nM, and kinetic titrations were performed. As a positive control, the first replicate series of GRFT injections was interleaved with concentration-matched injections of purified 6x-histidine-tagged GRFT obtained from Barry O'Keefe at the National Cancer Institute. Between each sample injection, the surface was regenerated with 10 mM glycine, pH 1.5, at 50 µL/min for 15 s and then re-equilibrated with PBS at 50 µLim·in for 2 min. Binding responses were adjusted by subtracting both the response observed on a blank sensor surface (activated and quenched without protein immobilization) and the response to zero-concentration samples. For His-GRFT, n=1 for all concentrations; for precipitation-purified GRFT, n=3 except for 12.5 nM, for which the second replicate showed no binding and was discarded. Kinetic constants for both precipitation-purified GRFT and His-GRFT were determined using Biaevaluation software (GE Healthcare Life Sciences, Marlborough, MA) by fitting a heterogeneous ligand model to each replicate dataset independently, then calculating means and standard deviations in the case of precipitation-purified GRFT.

Example 1: GRFT Production Targets and Existing Bioprocesses

To assess the challenges facing large-scale deployment of a GRFT-based microbicide in, we began by estimating targets for production cost and volumes. Referring now to FIG. 2, cost and sale for various GRFT manufacturing processes are described. Seven processes are plotted as a function of their potential production scale and cost. 1) (black diamond) a tobacco-based process based on Alam et al (half-open circle) an E. coli-based process using a conventional chromatography-based purification strategy and a lyophilized fast-dissolve insert (FDI) formulation, 3) (open circle) E. coli process using the same chromatography-based purification strategy and a gel formulation, 4) (black circle) E. coli-based process using the same chromatography-based purification strategy and a spray-dried FDI formulation, 5) (downward triangle) E. coli process with precipitation-based purification and lyophilized FDI formulation, 6) (open triangle) E. coli process with precipitation-based purification and gel formulation, 7) (upward triangle) E. coli process with precipitation-based purification and spray-dried FDI formulation.

Figure 3A:
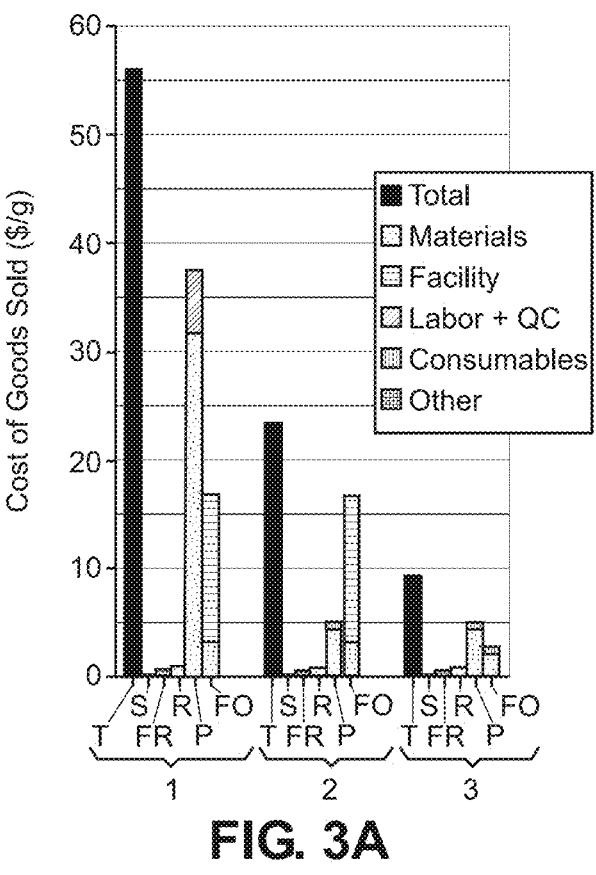
FIG. 3A-3E are graphs showing *E. coli*-based fermentation-based processes for GRFT manufacturing.

Thus, considering the predicted cost-effectiveness of a microbicide as one indicator of potential demand for it in a given setting. In the case of SARS-CoV-2, 1 billion doses per year can be met with the daily treatment of only 300 million patients, and 10s of tons of GRFT would be needed for widespread global deployment. We next compared these cost and volume targets to the capabilities of potential GRFT bioprocesses, including those previously demonstrated in engineered plants, as illustrated in FIG. 2. In order to meet both volumetric targets as well the standards of most biologics, purified GRFT must be free of viruses, greater than 99% pure, with less than 10 ng of contaminating DNA/dose, and endotoxin levels below 0.5 endotoxin units/mL. We analyzed the impact of the specific production of GRFT (g GRFT lg plant biomass), plant biomass costs, and the scalability of plant-based protein production on production volumes and costs. (XX-Refer to Supplemental Materials). We then compared this to a more traditional fermentation-based technology which was modelled using SuperPro Designer™, using previously reported downstream unit operations adapted as appropriate. For model details refer to Supplemental Materials. High level results of these analyses are given in FIG. 2. As can be seen from this analysis, plant based manufacturing would never be able to reach target production volumes for GRFT, whereas a more traditional fermentation based process such as using engineered E. coli (as illustrated in FIG. 3a) can easily hit these production scales (>20 tons annually).

Example 2: E. coli Based Fermentation Based Processes/or GRFT Manufacturing Model Referring specifically to FIG. 3, E. coli based fermentation based processes for GRFT manufacturing. FIG. 3A) A conventional E. coli based bioprocess reliant on three ion exchange chromatography steps for purification. The bioprocess begins with fermentation, followed by cell harvest via centrifugation, lysis via homogenization, centrifugation to clarify lysate and subsequent purification utilizing three ion exchange chromatography steps and two diafiltrations. FIG. 3I) In some aspects, an optimized E. coli based bioprocess, wherein precipitation is used in lieu of two ion exchange chromatography steps one diafiltration.

However, as also seen in FIG. 2, while fermentation-based processes can meet volumetric production requirements, standard process technology is unable to achieve cost targets of pennies/dose. In order to evaluate cost reduction opportunities, we performed sensitivity analyses on this bioprocess as illustrated in FIG. 3.

Figure 4A:
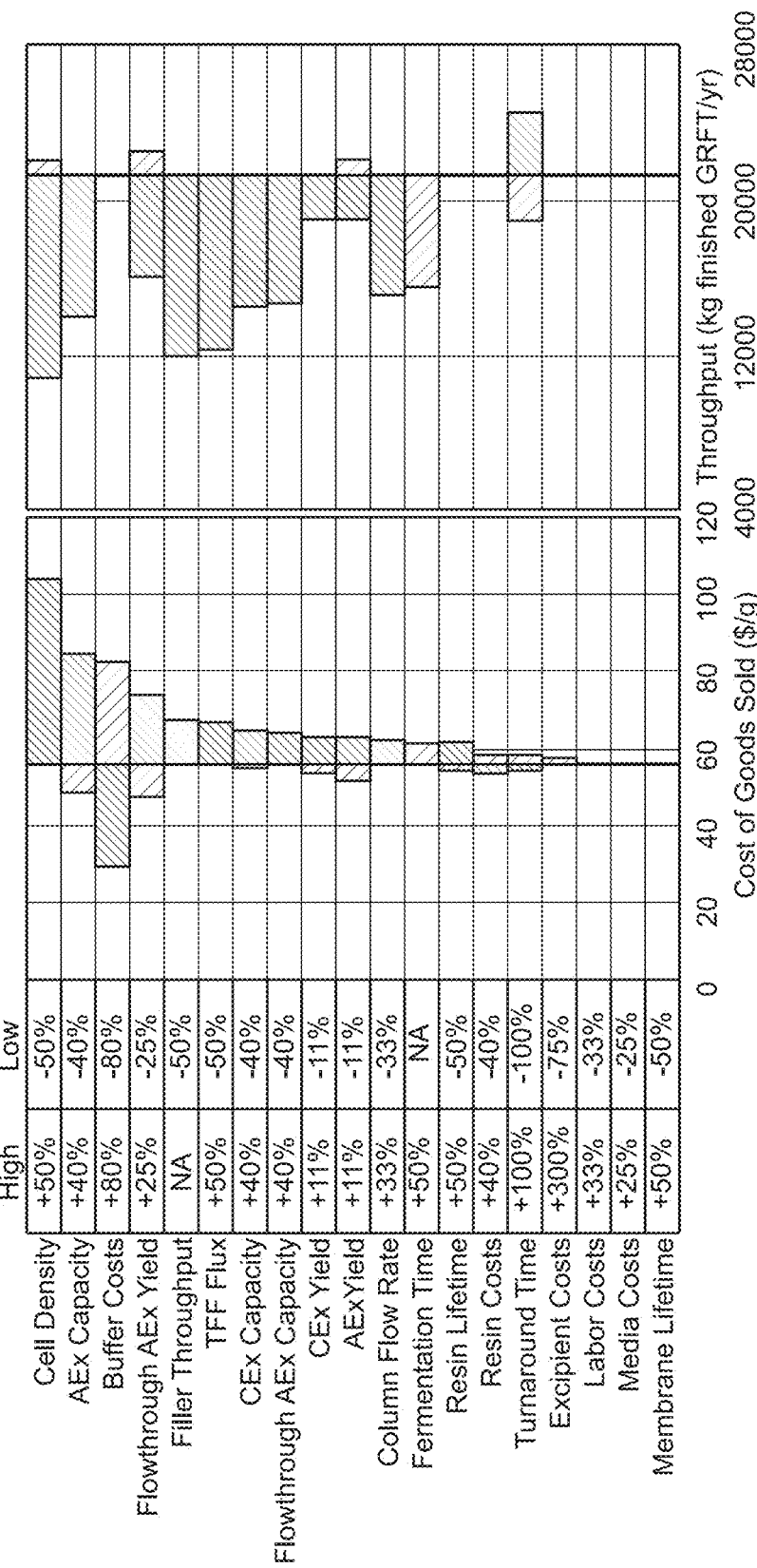
FIG. 4A-4C is a chart showing *E. coli*-based fermentation-based processes for GRFT manufacturing in accordance with one aspect of the present disclosure.
Figure 4B:
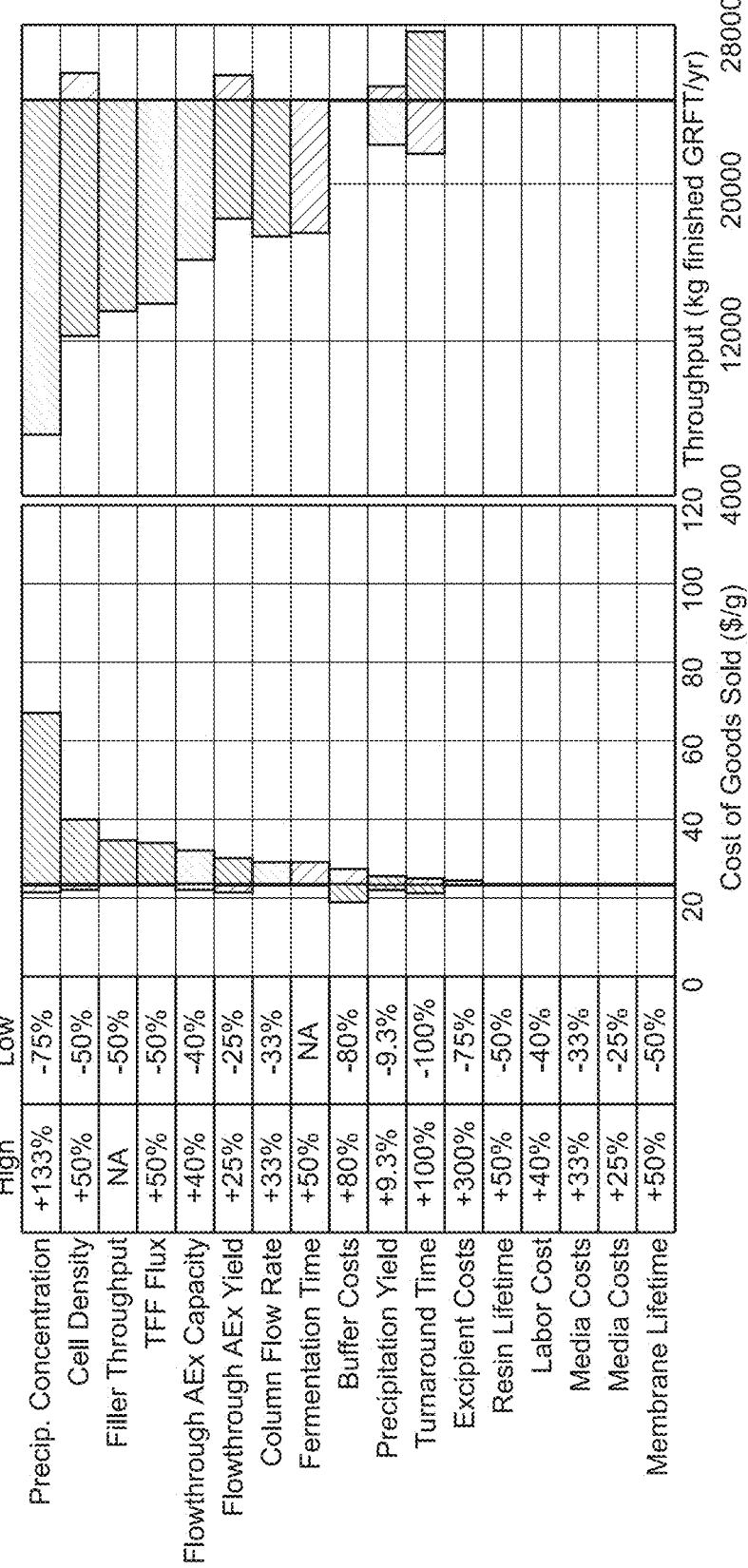
Figure 4C:
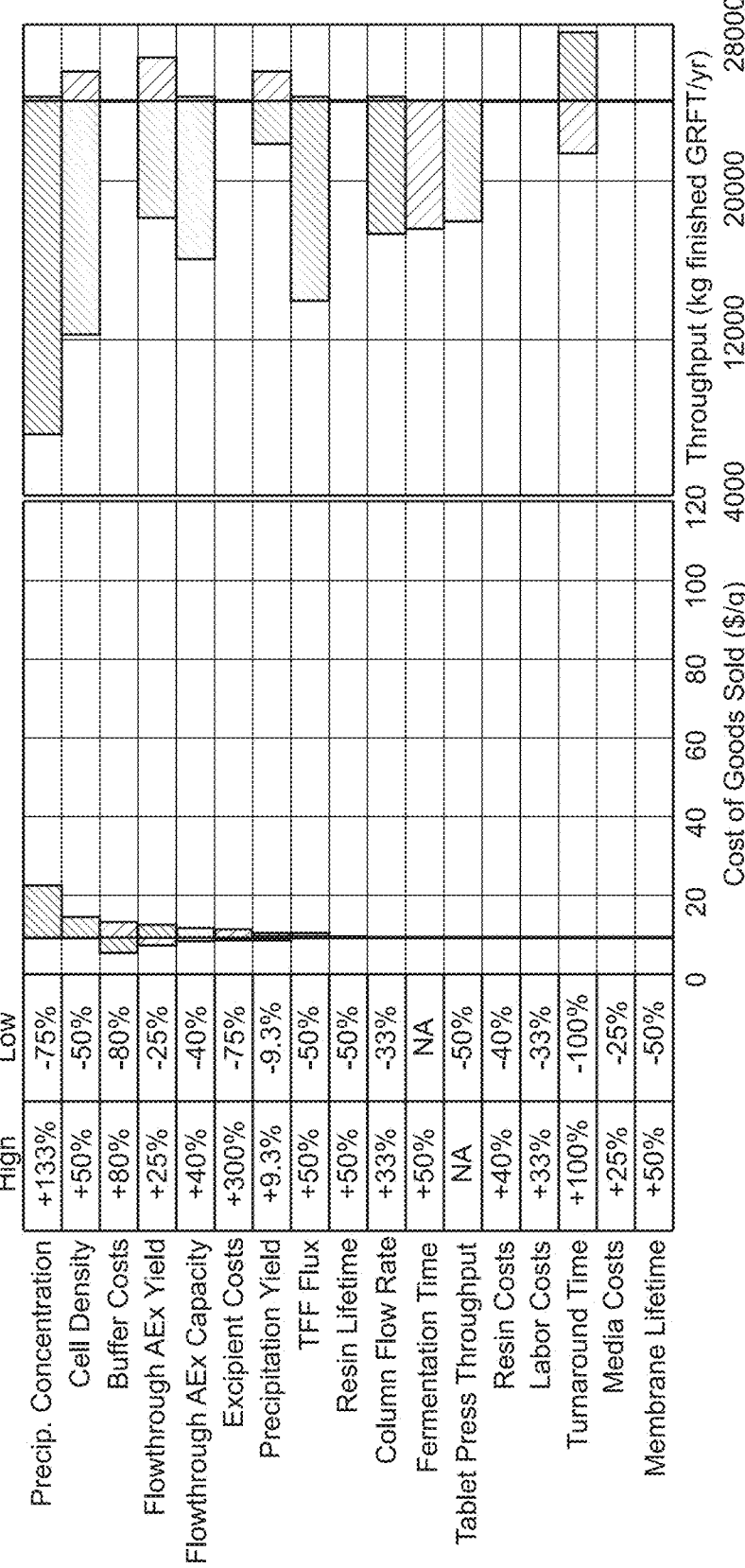

Referring specifically to FIG. 4, E. coli based fermentation based processes for GRFT manufacturing. FIG. 4A) A conventional E. coli based bioprocess reliant on three ion exchange chromatography steps for purification. The bioprocess begins with fermentation, followed by cell harvest via centrifugation, lysis via homogenization, centrifugation to clarify lysate and subsequent purification utilizing three ion exchange chromatography steps and two diafiltrations. FIG. 4B) an optimized E. coli based bioprocess, wherein precipitation is used in lieu of two ion exchange chromatography steps one diafiltration.

As can be seen in FIG. 4, from these results, not surprisingly, downstream recovery and purification (DSP) makes up from 40% to over 90% of the total manufacturing cost, consistent with most bioprocesses, and is the largest area for potential cost savings in the manufacturing of pharmaceuticals. The relative impact of DSP is even higher for larger scale bioprocesses where titers are high.

Figure 3B:
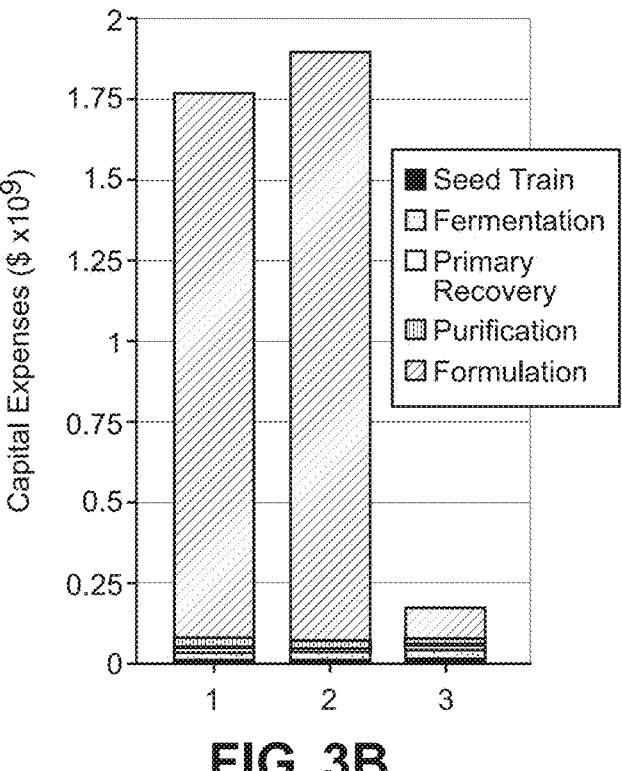
Figure 3C:
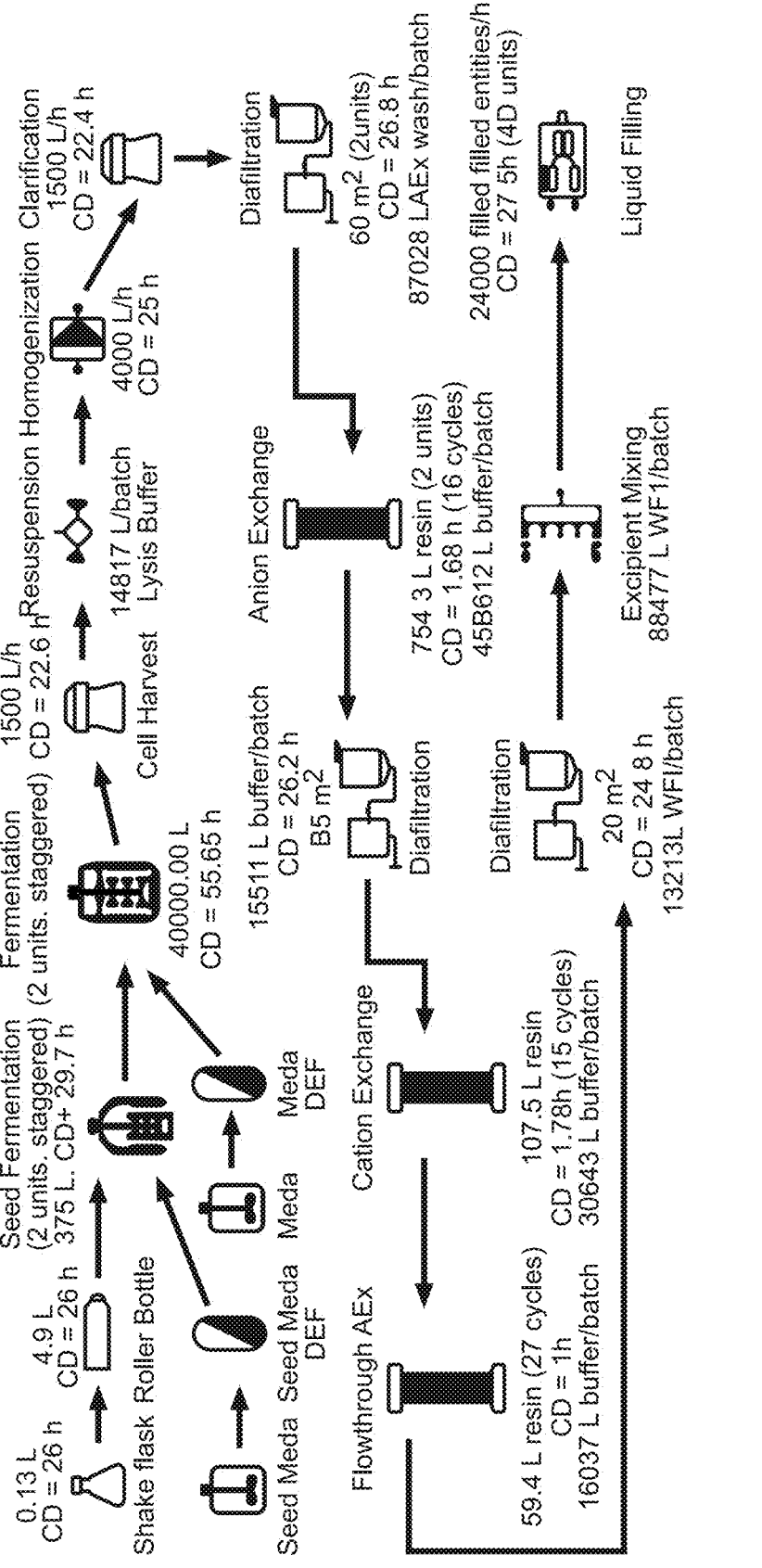
Figure 3D:
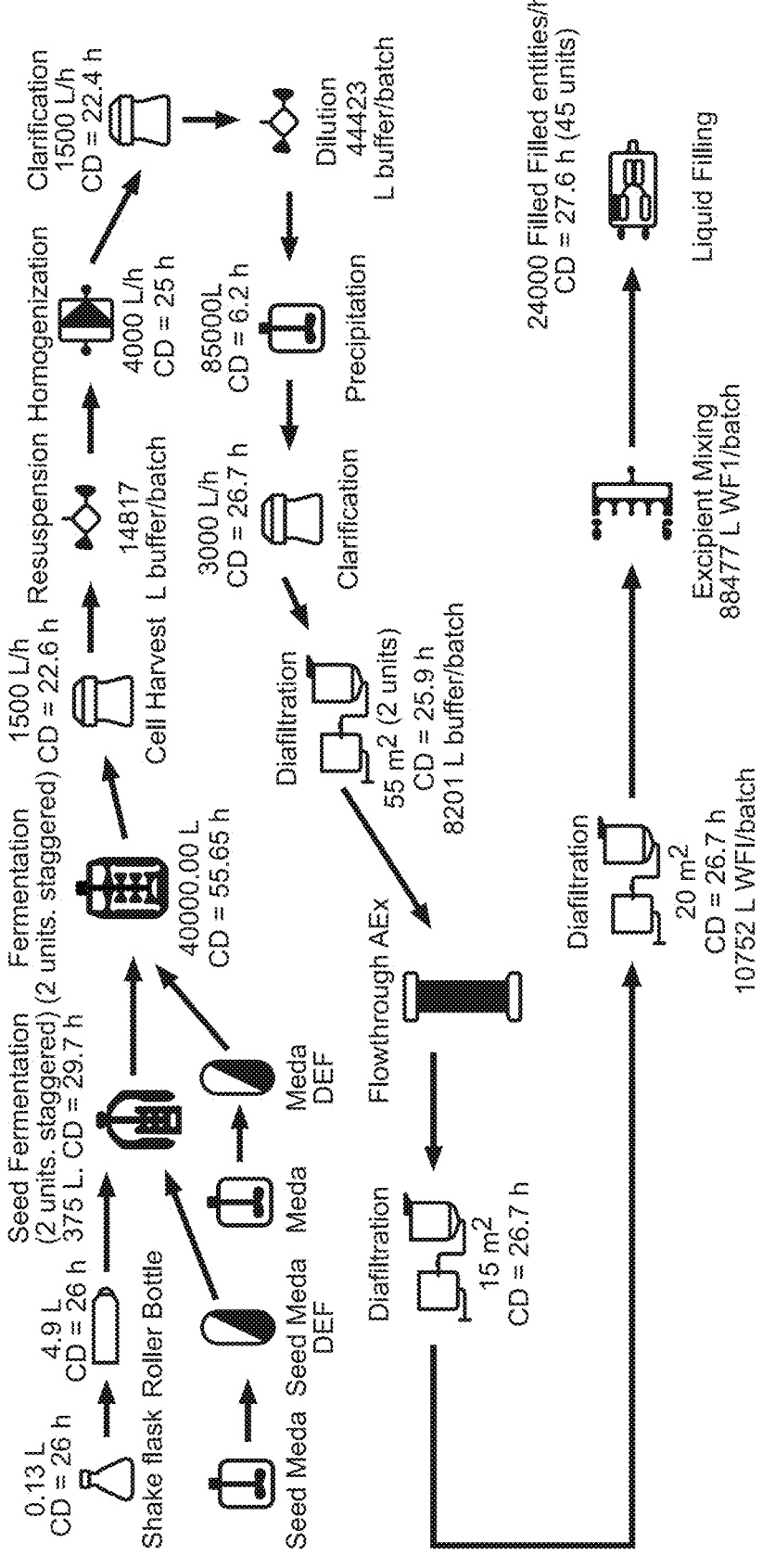
Figure 3E:
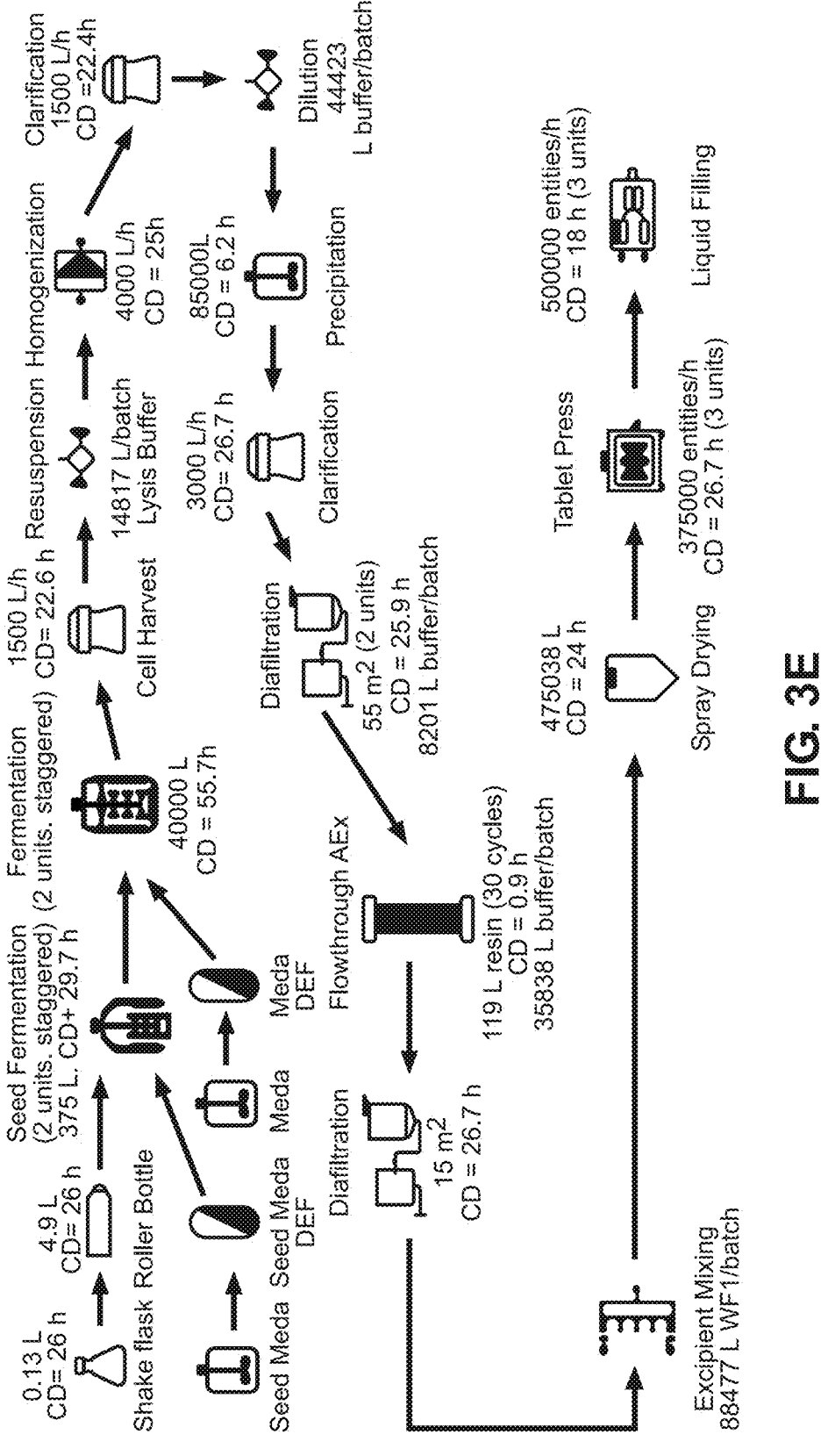

In order to reduce DSP costs and the number of unit operations we devised a potential bioprocess reliant on precipitation as the primary means of purification with only a final chromatographic polishing step as illustrated in FIG. 3B. The production costs for this potential process are anticipated to reach the target range as indicated in FIG. 3. The manufacture of GRFT has a unique potential in the proposed process, due to its unique biochemical properties including it thermostability and ease of heterologous expression.

Example 3: Development and Validation of Proposed Low-Cost Bioprocess

Figure 5:
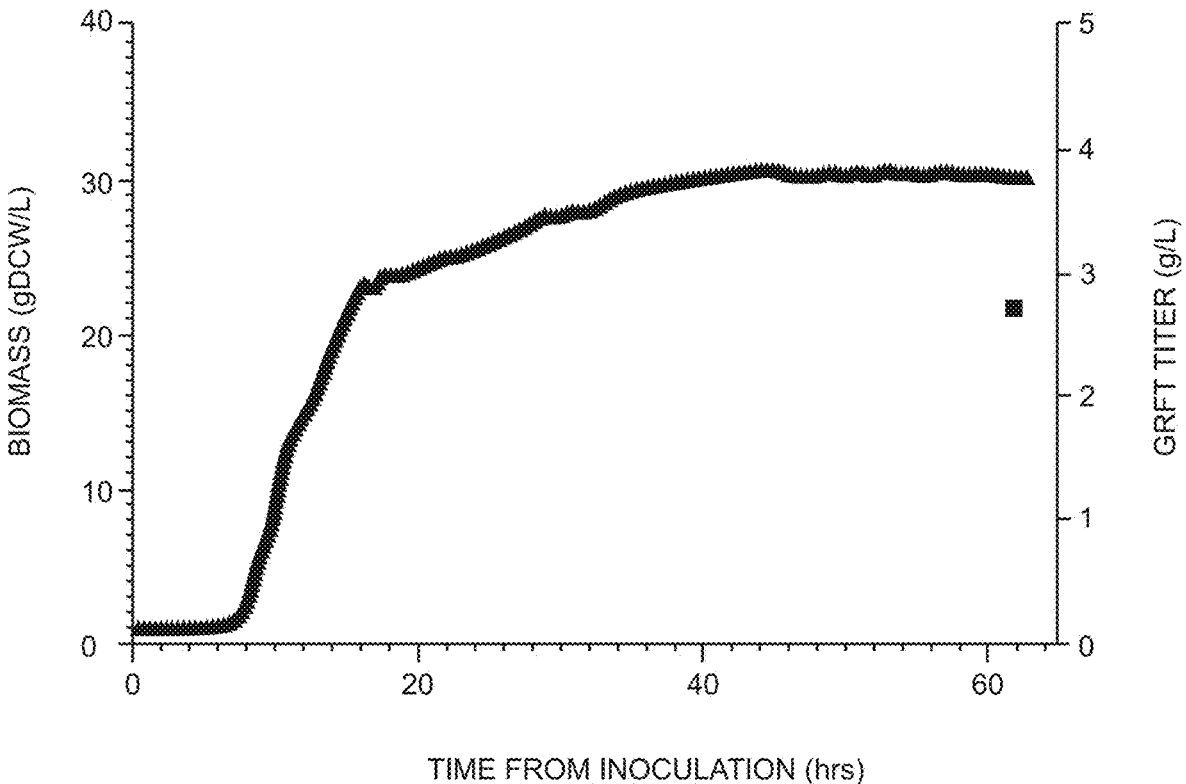
FIG. 5 is a graph showing the expression of GRFT in a two-state fermentation in accordance with one aspect of the present disclosure.
Figure 6A:
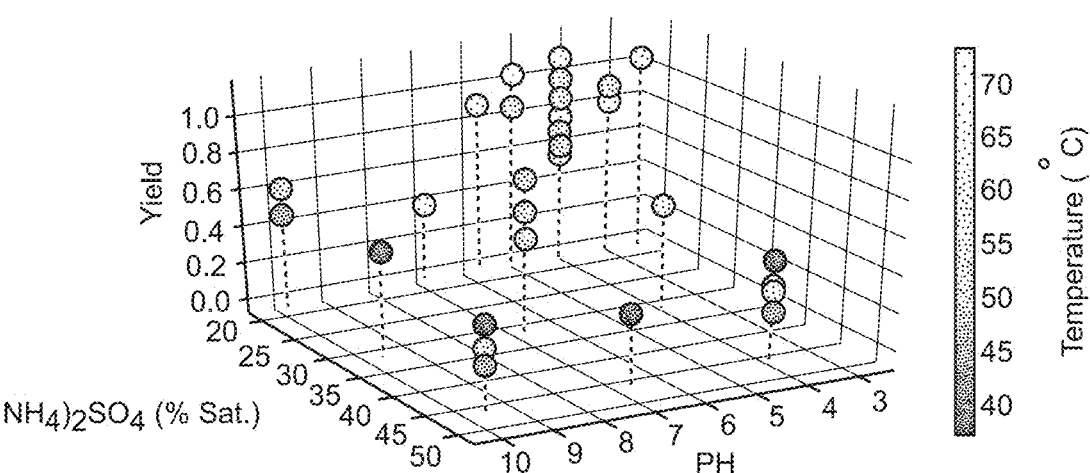
FIG. 6A-6D are graphs and SDS-PAGE gels showing the results of design of experiment studies to optimize the precipitation step in accordance with one aspect of the present disclosure.
Figure 6B:
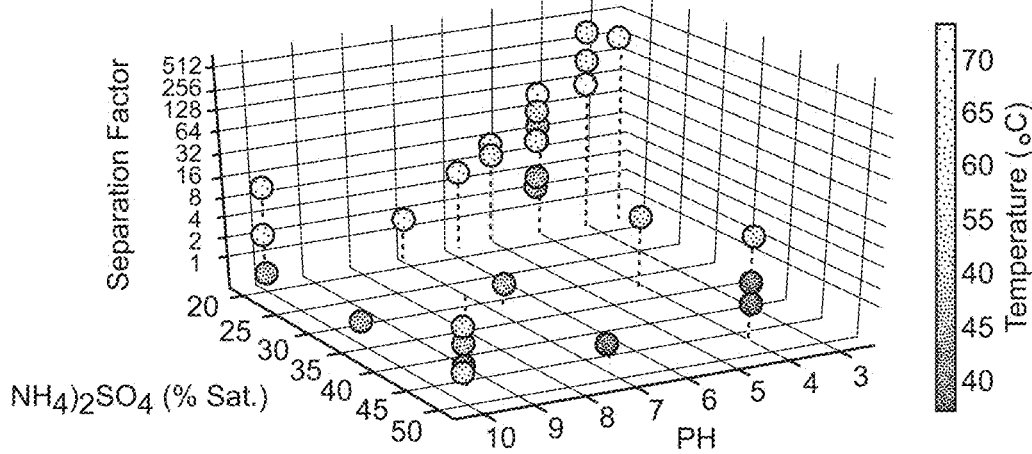
Figure 6C:
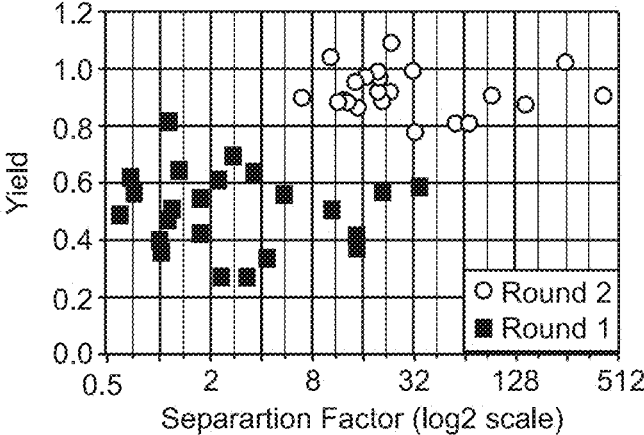
Figure 6D:
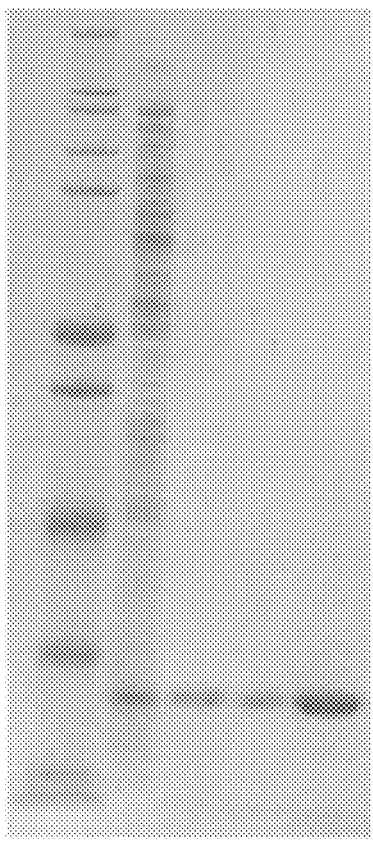
Figure 7:
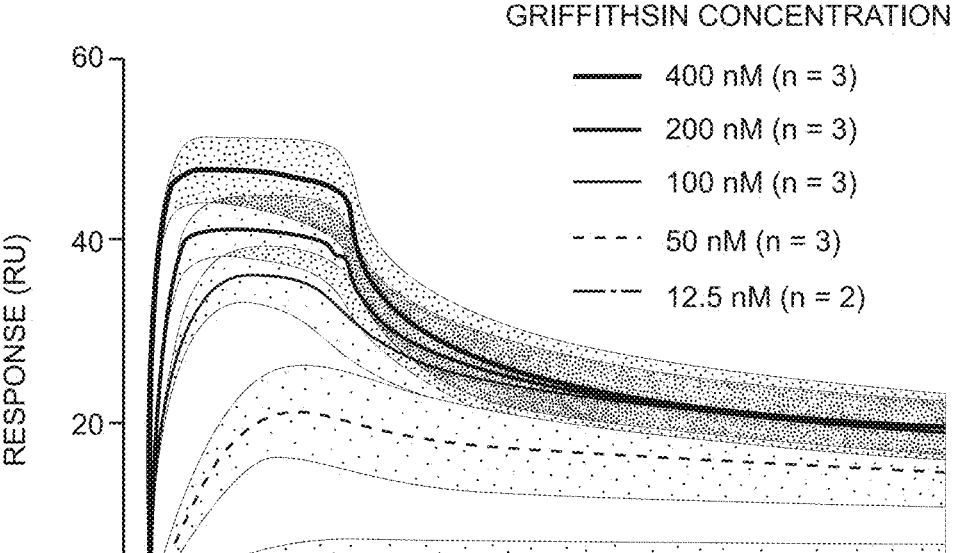
FIG. 7 is a graph showing the binding kinetics of purified GRFT v purified gp140 in accordance with one aspect of the present disclosure.
Figure 8:
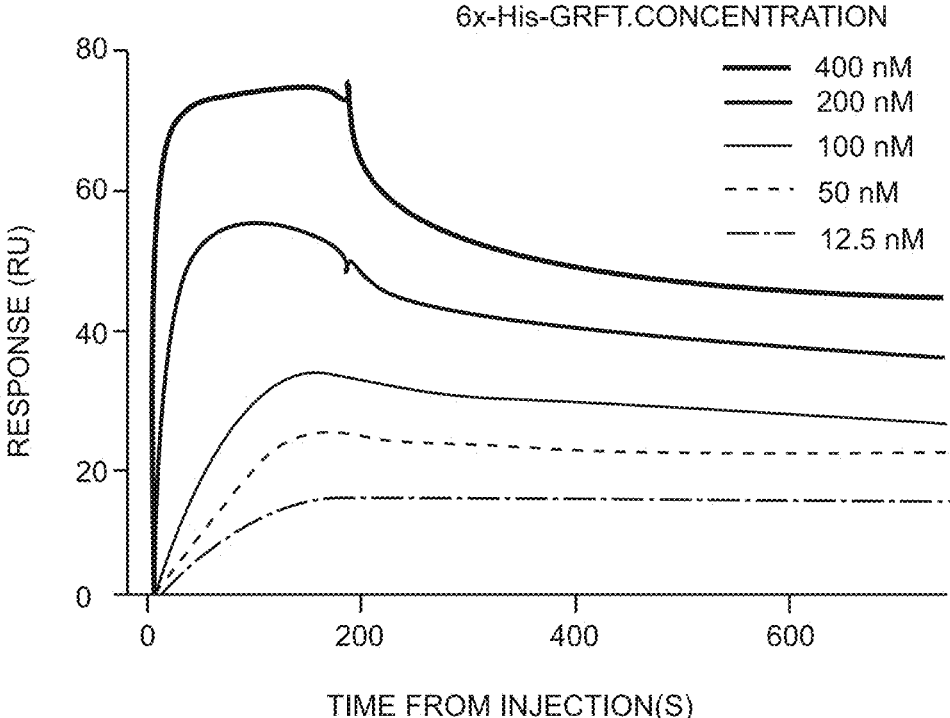
FIG. 8 is a graph showing 6x-GRFT SPR in accordance with one aspect of the present disclosure.
Figure 9:
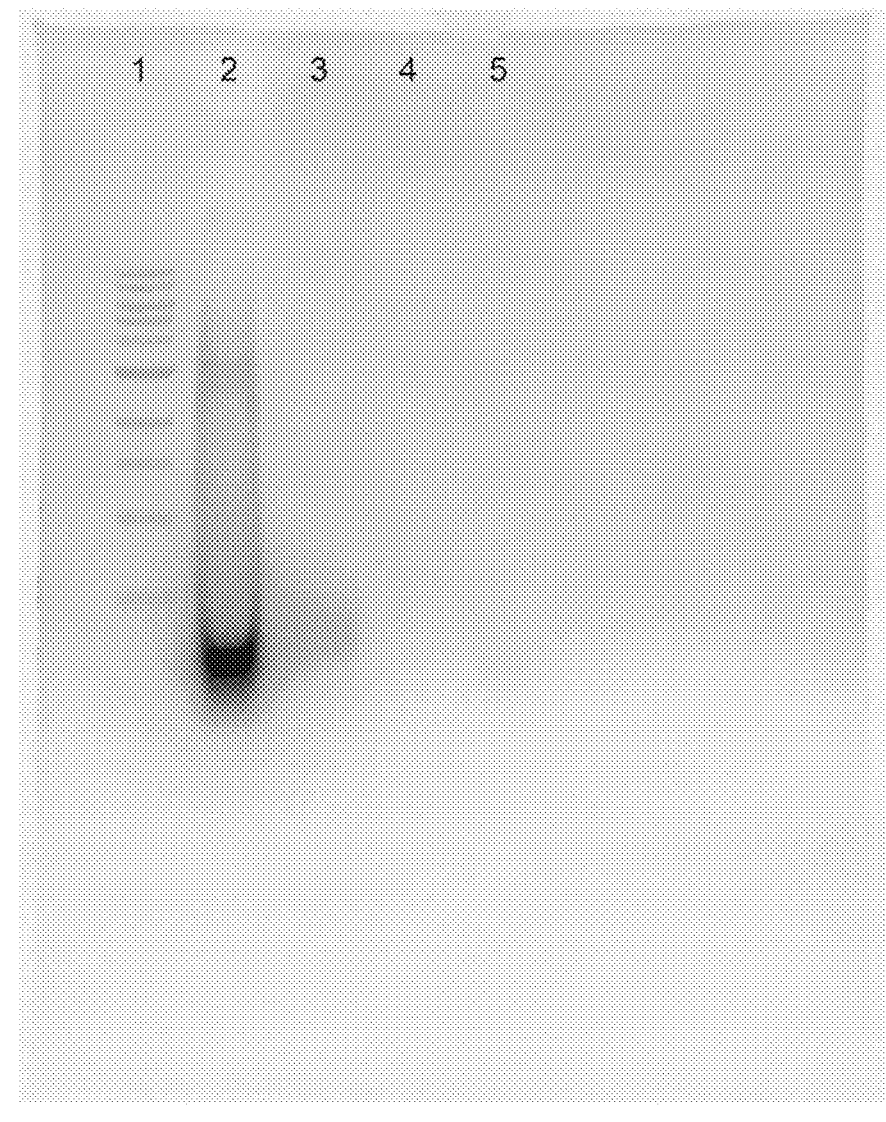
FIG. 9 is an SDS-PAGE showing determination of DNA content in precipitation-purified GRFT samples in accordance with one aspect of the present disclosure.

We next turned to the development and validation of our proposed low-cost bioprocess. Firstly, we expressed GRFT to relatively high titers in higher cell density minimal media fermentations. This was accomplished utilizing a two-stage production process as previously reported by Menacho-Melgar et al, wherein GRFT is expressed upon the entry of stationary phase, when batch phosphate is depleted. Specifically, the Griffithsin gene was cloned behind the well-known phoA gene promoter and evaluated for two stage production in bioreactors as illustrated in FIG. 5. Final biomass levels of ~30 gCDW/L supported GRFT titers as high as 2.7 g/L, in 60 hours.

Referring specifically to FIG. 5, Expression of GRFT in a two-stage fermentation. *E. coli* strain DLF_0025 containing GRFT under the control of the low-phosphate inducible promoter phoA was cultured in a 1 L bioreactor (Multifors 2, Infors-HT, Laurel, MD). Biomass levels are shown by black triangles and the final GRFT titer is shown by a gray square.

With the successful expression of GRFT to reasonable protein titers, we turned to development and optimization of the DSP, including a precipitation step. We leveraged standard Design of Experiments (DoE) methodology to optimize this process, with a focus on three key variables: pH, salt concentration (NH$_4$)$_2$SO$_4$ and temperature. In these experiments, GRFT was produced in shake flask cultures according to Menacho-Melgar et al. Cells were harvested, lysed by sonication and supernatants subjected to precipitation GRFT yield and purity were analyzed by SDS-PAGE and. Results are shown in FIG. 6.

Referring specifically to FIG. 6, Results of Design of Experiment studies to optimize the precipitation step. Three key variables were included in the DoE: temperature, ammonium sulfate concentration (% saturation) and pH. Two outputs were evaluated: yield (A) and separation factor (B). Gray dashed lines are included for perspective. C) A summary of these outputs over each experiment in the two rounds of DoE. D) Fluorescently stained SDS-PAGE gel converted to grayscale and with brightness values inverted for clarity. Lane 1, Mark 12™ unstained standard (ThermoFisher Scientific, Waltham, MA); Lane 2, untreated *E. coli* lysate containing GRFT (diluted 1:40); Lanes 3 and 4, supernatant following precipitation and supernatant following diafiltration into chromatography running buffer (each diluted 1:30); Lane 5, flow-through fraction from the final endotoxin removal chromatography step (diluted 5:8).

Elevated temperature, lower pH and low NHSO$_4$ concentrations gave the best results with respect to GRFT purity while maintaining reasonable yields. In the best conditions, we achieved a greater than 99% purity by SDS-PAGE, and a yield of 91%. In addition, after this simple precipitation, we were able to remove contaminating DNA leading to DNA undetectable levels by agarose gel electrophoresis. We then validated this process with GRFT produced from fermentations. Finally, residual endotoxin was removed by a single flow-through anion exchange chromatography step leading to endotoxin levels less than 50 endotoxin units per mL.

With the success in demonstrating a low-cost method to manufacture pharma-grade GRFT, we turned to evaluating its performance. To do this we evaluated in vitro binding to a purified HIV antigen (recombinant GP140), previously evaluated with purified GRFT. This was accomplished using SPR. Results are given in FIG. 6. K$_{on}$(association rate) and K$_{off}$ (dissociation rate) rates were measured to be 1.3±0.6× 10-7 and 6.4±5.2×10-2 respectively, resulting in an affinity of 4.4±1.6×10-9 M, matching well with previously reported measurement.

The GRFT bioprocess as described above represents an advance toward the low-cost high-volume production of this potential antiviral prophylactics and therapies. The process relies on non-specific precipitation of contaminating cellular proteins to greatly minimize DSP costs. As mentioned above, this approach uniquely leverages the thermostability of GRFT. The use of optimal precipitation is critical to reducing overall process costs and the cost of the API.

Example 4: *E. coli* Fermentation-Based GRFT Bioprocess Models—Additional Variations General Design Considerations Here we present several variations on a batch bioprocess design for GRFT production by *E. coli* fermentation. Each process is designed such that batch throughput and cycle time are limited by the production fermentation procedure and other equipment is sized to meet the consequent material or throughput demands without excess capacity. Maximum feasible equipment capacities or throughputs were set according to default SuperPro options, except where noted. To account for processing delays and operations not included in the model, a minimum of 4 hours is allowed between operations for consecutive batches in each piece of equipment. The plant is assumed to be operational for 85% of each year. Each process comprises five main sections: seed train, fermentation, primary recovery, purification, and formulation. Additionally, we modeled two different purification scenarios and three different formulation scenarios, for a total of 6 baseline models. We then conducted sensitivity analyses on key parameters of each of the 6 models, as described below.

Seed Train

300 L of inoculum are needed per batch to support production-scale fermentation. This inoculum is prepared in three steps of 10-fold scale increases: each batch begins when a 30 mL shake flask culture is inoculated from frozen stock; a 3 L roller bottle culture is then inoculated from the shake flask; and finally a 300 L stainless steel seed fermenter is inoculated from the roller bottle. Seed fermenter media is prepared in a separate stainless steel tank and sterilized by dead end filtration (DEF). Each seed culture is allowed to grow for 24 hours, and one hour is allowed for each transfer of media or culture from vessel to vessel. While the first two cultures take place in disposables, clean in place (CIP) and steam in place (SIP) operations are required for the seed fermenter and cause its cycle time to slightly exceed the batch cycle time. Thus, two seed tanks are run in staggered mode to avoid cycle time increases. Seed train operations require a total of approximately 79 hours in each batch.

Fermentation

Production-scale fermentation takes place in two stainless steel tanks each holding 30000 L and operating on a staggered schedule. Media for these tanks is prepared in a separate stainless steel blending tank and sterilized by DEF. With a two-stage fermentation in which the culture grows to a density of 100 grams dry cell weight per L (gDCW/L) within 24 hours and protein is expressed during stationary phase, the yield of biomass from glucose is assumed to be 43%. With 48 hours of fermentation time in addition to CIP/SIP and material transfer operations, the fermentation procedure is the longest in the batch at 56 hours. Thus, with two fermenters operating on a staggered schedule, the minimum process cycle time is 28 hours in all models. All other unit procedures are designed so that their procedure cycle times do not exceed this limit, to avoid lengthening the process cycle time. Fermentation media preparation begins with 74 hours elapsed in the batch, and the section ends with the conclusion of tank SIP/CIP operations at approximately 130 hours elapsed.

Primary Recovery

After each fermentation, the 30000 L culture is harvested by disk-stack centrifugation at a flow rate of 1500 L/h. It is assumed that all biomass is recovered in a volume of approximately 15000 L. The cell slurry is then diluted back to 30000 L by the addition of lysis buffer before high-pressure homogenization. Homogenization is achieved by 3 passes with a pressure drop of 700 bar and a flow rate of 4000 L/h; it is assumed that 99% of cell contents are released and protein denaturation is not considered. The composition of cell dry weight is assumed to be 5% GRFT, 45% host cell proteins (HCPs), 20% nucleic acids, 12% lipopolysaccharide (LPS), and 18% other insoluble debris. Primary recovery continues with another centrifugation step to remove insoluble cell debris, again at a flow rate of 1500 L/h. All debris is removed, with negligible volume change or loss of other cell components. Cell harvest begins with 127 hours elapsed in each batch, and CIP/SIP operations in the lysate clarification centrifuge conclude at 192 hours elapsed.

Purification

The purification section is design to produce GRFT bulk drug substance (BDS) with the following purities relative to three major categories of contaminants: for HCPs, <100 ppm31; for nucleic acids, <10 ng per dose32, i.e. <2.5 ng/mg GRFT; and for LPS, <4.5 ng/mg GRFT, assuming a limit of 5 EU/kg patient bodyweight, a minimum patient weight of 36 kg, and a mass of 100 pg LPS per EU. Considering the cell composition given above, the total-process minimum separation factors (a) needed for HCPs, nucleic acids, and LPS are 90000, 1600000, and 498000, respectively. We modeled two different purification scenarios to achieve these targets: a process based on a precipitation step followed by one diafiltration step and one chromatography step; and a conventional process based on three chromatography steps and two diafiltration steps.

For all diafiltration steps in all models, tangential flow filtration (TFF) with a filtrate flux of 30 L/m2-h, a retention coefficient of 0 for buffer salts and 1 for all macromolecules, constant-volume operation, membrane replacement every 1000 operating hours, and a maximum membrane area per skid of 100 m². For all chromatography steps in all models, we assume a constant flow rate of 300 cm/h, a bed height of 250 cm, a maximum column diameter of 2 m, and resin replacement every 100 cycles. For anion and cation exchange columns operated in bind-and-elute mode, a total loading capacity of 100 g/L and 120 g/L, respectively. Both kinds of columns are sized to accommodate the interaction with the resin of 100% of each of the four macromolecular species (GRFT, HCPs, nucleic acids, and LPS) present in the feed. All bind-and-elute chromatography procedures include equilibration with 6 BVs of loading buffer, loading, washing with 5 bed volumes (BVs) of loading buffer, elution with 4 BVs of elution buffer (of which the eluate is recovered in 2 BVs), and regeneration with 4 BVs of regeneration buffer. For flow-through chromatography, the wash and elution steps are omitted and size the column to accommodate the bound species that demands the highest capacity (i.e., that has the highest value of mass in feed divided by species-specific loading capacity).

The precipitation-based purification process begins with a 2.5-fold dilution of the clarified cell lysate from 50 g/L total protein to the precipitation working concentration of 20 g/L. The result is approximately 75000 L of lysate per batch at pH 3.4 and an $(NH_4)_2SO_4$ concentration of 0.82 M (20% saturated at 25° C.). The diluted lysate is transferred to an 83000 L stainless steel tank and heated to 60° C. over 30 minutes, then held at 60° C. and stirred for an additional 30 minutes. During this time contaminants are precipitated with the following separation factors, as demonstrated at lab scale for our optimized precipitation step: 426 for HCPs (FIG. 5), 1000 for LPS (as measured by Pierce™ Chromogenic Endotoxin Quant Kit; Thermo Fisher Scientific, Waltham, MA; data not shown), and 14400 for DNA. To meet final purity targets, the remaining purification steps in this scenario must therefore provide additional separation factors of >211, >498, and >111 for HCPs, LPS and nucleic acids, respectively.

The remaining separations are achieved by a single flow-through strong anion exchange chromatography step. We follow the method of Chen et al., in which a pH between the isoelectric points of GRFT (5.4) and LPS (approximately 2) causes both LPS and nucleic acids to be attracted to the resin far more strongly than are proteins, while 50 mM $(NH_4)_2SO_4$ is used to screen charge attractions between proteins and these other contaminants. In our hands, and consistent with the findings of Chen et al., a version of this procedure at lab scale provided an a for LPS of approximately 1000. Because the charge attraction of nucleic acids to the resin should be even greater than for LPS, this step achieves an a of 1000 for both contaminants in the model. Finally, a relatively large a for HCPs can also be achieved in this step, on the basis that the HCP load at this point will be very highly mono dispersed. Achieving a large a therefore only requires that conditions can be tailored to resolve GRFT from one or a very few distinct HCP species, which may be especially feasible if yield is allowed to decrease somewhat so that fractions can be collected more selectively. Eluate from this procedure contained no detectable HCP contaminants (FIG. 5D). Therefore, a GRFT yield of 80% and an a for HCPs of 225 is achieved for this step.

Between the precipitation treatment and the final chromatography step, precipitate clearance and buffer exchange are required. After the precipitation treatment, the suspension is transferred to a disk-stack centrifuge operating at a flow rate of 3000 L/h. 100% removal of precipitates, with a consequent reduction in volume to about 71000 L. The process stream is then transferred to a TFF procedure for diafiltration and concentration. To minimize the buffer volume used in diafiltration and loading for the final chromatography step, as well as the membrane area needed for diafiltration, the feed is first concentrated to a total protein concentration of approximately 50 g/L (26-fold concentration in the baseline model). The approximately 2700 L of concentrated feed are then diafiltered. Reducing the $(NH_4)_2SO_4$ concentration from the 0.82 M used in the precipitation step to the 0.05 M needed for the flow-through chromatography step requires processing 3 diafiltration volumes. Given the general TFF assumptions stated above, completing these steps without an increase in the batch cycle time requires two TFF skids running in parallel with 55 m² of membrane each.

Finally, the 2700 L process stream is loaded onto a strong anion exchange column for flow-through chromatography, which proceeds as previously described. A loading capacity of 0.09 g/L for LPS33 and 6-12 g/L for nucleic acids. Given the material load in the feed and the limits on column size and binding capacity, running this procedure in one cycle would require approximately 3600 L of resin spread across 5 columns of 1.9 m diameter. The procedure is instead modeled as using one 0.78 m diameter column, with the feed stream split into sub-batches and processed in 30 cycles of just over 50 minutes each. The precipitation-based purification scenario ends with a total of 2700 L of GRFT BDS per batch collected from the column, containing 40 g/L GRFT, 3.78 mg/L HCPs (94.5 ppm), 95 µg/L LPS (2.4 ng/mg GRFT; 96 EU/dose), and 11 µg/L nucleic acids (0.275 ng/mg GRFT; 1.1 ng/dose). From the beginning of lysate dilution in precipitation buffer at 187 hours elapsed to the end of regeneration and equilibration operations in the flow-through chromatography procedure at 265 hours elapsed, the precipitation-based purification section requires a total of 78 hours. The overall yield of the precipitation-based process is 73.2%.

The conventional purification process begins with TFF diafiltration of the clarified cell lysate from lysis buffer into anion exchange loading buffer. We assume that 95% buffer exchange (3 diafiltration volumes) is sufficient for this step, given a lysis buffer that is relatively dilute and of a similar pH to the anion exchange loading buffer. Completing this step without an increase in the batch cycle time requires two TFF skids with 60 m² of membrane each.

Next, the filtrate is loaded onto a strong anion exchange column running in bind-and-elute mode. At a moderately basic pH, LPS and nucleic acids should have much higher densities of negative charge than GRFT and most HCPs; they should therefore interact much more strongly with the resin, and an a of 1000 for both nucleic acids and LPS. For HCPs, an a of 20 based on the similarity of GRFT's isoelectric point (5.4) to that of many *E. coli* proteins and based on typical values from the literature. The procedure requires two 1.96 m diameter columns running in parallel, with the feed stream split into sub-batches and processed in 16 cycles. We assume 90% yield of GRFT, recovered in 2 BVs per cycle or approximately 48000 L total.

The eluate from the first anion exchange step must next be concentrated and diafiltered in preparation for a cation exchange step. The feed is first concentrated to a total protein concentration of approximately 50 g/L (12.5-fold concentration from the eluate in the baseline model). The approximately 3900 L of concentrated feed are diafiltered with 4 diafiltration volumes to achieve >98% buffer exchange, which may be necessary when switching from a salty, basic anion exchange elution buffer to a dilute, acidic cation exchange loading buffer. Completing these steps without an increase in the batch cycle time requires one TFF skid with 85 m² of membrane. The resultant feed stream is then loaded onto a strong cation exchange column under bind-and-elute conditions. Because GRFT will be attracted to LPS and nucleic acids by its opposite charge under cation exchange conditions, relatively little separation of GRFT from these components in this step, with a=2. An a of 20 for HCPs, as with the first anion exchange step. This procedure is nm in one column of 0.74 m diameter with the feed stream split into 15 consecutively-processed sub-batches. As before, 90% yield of GRFT recovered in 2 BVs per cycle, or approximately 3300 L per batch.

The final step in the conventional purification process is flow-through strong anion exchange chromatography, as described for the precipitation-based purification scenario. Under the conditions we have described thus far, the eluate from the cation exchange step contains approximately 35.5 g/L GRFT, 0.8 g/L HCPs, 0.09 g/L LPS, and 0.14 g/L nucleic acids. Assuming that GRFT can be eluted from the cation exchange column using an acidic buffer containing 50 mM $(NH_4)_2SO_4$, the cation exchange eluate can be loaded directly onto the flow-through column. As before, a GRFT yield of 80%, collected after the column in a total volume of approximately 3300 L. The eluate is GRFT BDS with a composition of 28.7 g/L GRFT, 34 µg/L LPS (1.2 ng/mg GRFT; 48 EU/dose), 57 µg/L nucleic acids (2 ng/mg GRFT; 8 ng/dose), and just under 2.9 mg/L HCPs (100 ppm). The conventional purification process begins with 189 hours elapsed in each batch and concludes with 316 hours elapsed. The overall yield of the conventional process is 64.8%.

Formulation and Finishing

For each purification scenario we also model the production of three different formulations, each containing 4 mg GRFT: a 4 mL gel dispensed from a single-dose applicator; a fast-dissolve insert (FDI) prepared by lyophilization directly in tablet molds; and a second FDI that is prepared by spray drying followed by tablet pressing but is otherwise identical to the first. The compositions and processes for both the gel and the FDI are the same as those reported for recent studies of GRFT in non-human primates.

Following collection of GRFT BDS from the flow-through anion exchange procedure at the end of both purification scenarios, all three formulation scenarios begin with the diafiltration of this BDS into water for injection (WFI). 98% buffer exchange, accomplished in 4 diafiltration volumes. Because of slight differences in the volume of GRFT BDS generated, this requires 20 m² of membrane under the conventional purification scenario but only 15 m² under the precipitation-based scenario. After diafiltration, all three formulation scenarios likewise proceed with the addition of excipients and dilution to final concentrations in WFI. For the gel, the mass fractions of excipients are 3% carrageenan, 0.35% sodium chloride, 0.26% sodium acetate trihydrate, and 0.2% methylparaben. The gel requires a final GRFT concentration of 1 g/L (very nearly 0.1% w/w); after the addition of excipients and a final dilution in WFI, this gives final formulated mug product volumes of 95000 and 107000 L per batch under the conventional and precipitation-based purification scenarios, respectively. The FDIs are more concentrated with 4 mg GRFT per 128 mg FDI, or 3.125% w/w.15 The remainder of the FDI weight is 7.75% sucrose, 11.625% carrageenan, 31% dextran, and 46.5% mannitol. Accounting for the concentration that will occur upon drying, the concentration of GRFT after addition of excipients and before drying is 0.45% w/w in both FDI scenarios. This gives final pre-drying volumes of 20600 and 23300 L per batch under the conventional and precipitation-based purification scenarios, respectively. We estimate the following prices for excipients: carrageenan, $11/kg; dextran, $40/kg; mannitol, $15/kg; methylparaben, $7/kg; sodium acetate, $0.45/kg; sucrose, $0.80/kg.

In a lyophilized FDI scenario, drying is preceded by filling of the formulated product stream into tablet molds such that FDI tablets are formed during drying; sealing of these molds after drying would give a final packaged product. Drying in individual molds is necessary because lyophilization tends to produce large cakes of dry material, which would be too cumbersome to handle for post-drying milling and tableting. At the GRFT concentration of 0.4534% w/w after excipient mixing, each mold must be filled with approximately 882 mg of pre-drying material. Accounting for 2 hours total for material transfer into and out of the dryers, the maximum drying time that can be accommodated without increasing the batch cycle time is 25.5 hours. By comparison, the process used by Lal et al. took a total of 30 hours, including 27 for primary and secondary drying. At baseline, we assume a 25.5 hour drying time.

In the spray-dried FDI scenario, drying proceeds immediately after excipient mixing. This is possible because spray drying, unlike lyophilization, can directly produce fine powder that is suitable for tablet pressing. We assume a volumetric drying rate of 2 kg m$^{-3}$ h$^{-1}$ based on vendor information. Completion of drying without increasing the batch cycle time requires a single dryer with 424000 L or 475000 L of drying volume (6 m or 6.35 m diameter, 15 m height) under the conventional and precipitation-based purification scenarios, respectively. The residual volatiles level is again assumed to be 0.5%. After drying, the resulting powder is pressed into tablets. Rotary tablet presses are available with throughputs of up to 500000 tablets per hour, providing an advantage for the spray-drying scenario over the liquid filling operations of the other two formulation scenarios. Under the conventional purification scenario, two presses running in parallel with throughputs of 500000 tablets per hour are required to process the dried product stream without a batch cycle time increase. Under the precipitation-based purification scenario, three parallel presses with throughputs of 375000 tablets per hour are required. In both the spray-dried and lyophilized FDI scenarios, the final product streams are approximately 24000000 tablets (3060 kg) or 27000000 tablets (3460 kg) per batch under the conventional and precipitation-based purification scenarios, respectively.

The ending times for the formulation section, and therefore the batch, are as follows under the conventional and precipitation-based purification scenarios, respectively: for the gel, 336 or 317 hours elapsed; for the lyophilized FDI, 391 or 341 hours elapsed; for the spray-dried FDI, 408 or 353 hours elapsed.

Auxiliary Operations

All non-disposable equipment, except chromatography columns, undergoes CIP and SIP operations once per batch. CIP cycles take 110 minutes and include three rinses with WFI as well as one rinse each with acid and base. SIP cycles are assumed to take 50 minutes with 30 minutes of steaming. The cost of CIP skids, but not SIP panels, is included according to built-in cost models based on the volumes of cleaning solutions required. All waste disposal costs are assumed to be $0.01/kg waste. For simplicity, some other auxiliary operations and equipment categories are omitted from the models. Buffer preparation and transfer would require dedicated tanks, piping, labor, and materials storage. Rather than modeling these aspects explicitly, we use a baseline estimate of $5/L for each buffer to account for all associated costs. Likewise, we omit the additional tank capacity and transfer steps that typically would be needed to hold in-process material pools between major unit procedures (e.g., to hold chromatography eluate before transfer to a filter).

Economic Considerations

The potential of GRFT-based microbicides are an important part of the HIV prevention portfolio in low-resource settings in the future, we consider only large-scale production (1000-20000 kg GRFT/yr) with a requirement for relatively low profit margins.

One skilled in the art will readily appreciate that the present disclosure is well adapted to carry out the objects and obtain the ends and advantages mentioned, as well as those inherent therein. The present disclosure described herein are presently representative of preferred aspects, are exemplary, and are not intended as limitations on the scope of the present disclosure. Changes therein and other uses will occur to those skilled in the art which are encompassed within the spirit of the present disclosure as defined by the scope of the claims.

The complete disclosure of all patents, patent applications, and publications, and electronically available material cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

The invention claimed is:

1. A method of producing Griffithsin comprising:

i) providing a genetically modified *E. coli* microorganism comprising a gene encoding a Griffithsin protein operably linked to an inducible promotor;

ii) growing the genetically modified microorganism under conditions that induce the promotor and cause expression of Griffithsin, the inducible promotor expresses the Griffithsin protein when phosphate is depleted from media in which the genetically modified microorganism is growing;

iii) releasing Griffithsin from the microorganism by cellular disruption;

iv) performing a precipitation step to remove contaminating protein and nucleic acids;

v) performing an anion exchange chromatography step, wherein the precipitation step and anion exchange chromatograph step produce purified Griffithsin, and wherein the Griffithsin is a protein of the red algae Griffithsia.

2. The method of claim 1, wherein Griffithsin gene is SEQ ID NO: 1.

3. The method of claim 1, wherein cellular disruption occurs by sonication or cellular lysis.

4. The method of claim 1, wherein the precipitation step is performed at a temperature greater than 55° C. and less than 73° C.

5. The method of claim 1, wherein the precipitation step is performed at a temperature of 55° C.

6. The method of claim 1, wherein the precipitation step further comprises heating to effect precipitation between 5 and 60 minutes.

7. The method of claim 1, wherein the precipitation step further comprises maintaining a pH greater than 2.5 and less than 4.

8. The method of claim 1, wherein the precipitation step occurs in the presence of at least 0.8M $(NH_4)_2SO_4$.

9. The method of claim 1, wherein the precipitation step occurs in the presence of between 0.8M and 1.4 M $(NH_4)_2SO_4$.

10. The method of claim 1, wherein the precipitation step further comprises a centrifugation step.

* * * * *

SEQUENCE LISTING

<160> NUMBER OF SEQ ID NOS: 1

<210> SEQ ID NO 1
<211> LENGTH: 2395
<212> TYPE: DNA
<213> ORGANISM: Artificial Sequence
<220> FEATURE:
<223> OTHER INFORMATION: Synthetic plasmid

<400> SEQUENCE: 1

```
gttaatcttt tcaacagctg tcataaagtt gtcacggccg agacttatag tcgctttgtt      60
tttatttttt aatgtatttg tatctagaga ttaaagagga gaatactaga tgatgtcttt     120
aacccaccgt aaatttggtg gatccggtgg ttcacctttt agtggattat cgtctattgc     180
ggtgcgctct ggctcgtact tagatgcaat catcattgat ggagtacacc atggcggctc     240
```

-continued

```
cggcggcaac ctgtcgccta ctttcacttt tggcagtggg gagtatatta gcaatatgac      300
catccgctcg ggtgattata ttgacaatat cagctttgag acgaatatgg ggcgtcgttt      360
cggcccatac ggagggtcgg gtggttcggc taatacgctg tccaatgtaa aggtaatcca      420
aattaatggc tccgctggcg actatcttga ttcgttggac atttattatg aacaatattg      480
accaggcatc aaataaaacg aaaggctcag tcgaaagact gggcctttcg ttttatctgt      540
tgtttgtcgg tgaacgctct ctactagagt cacactggct caccttcggg tgggcctttc      600
tgcgtttata gacgaattct ctagatatcg ctcaatactg accatttaaa tcatacctga      660
cctccatagc agaaagtcaa aagcctccga ccggaggctt ttgacttgat cggcacgtaa      720
gaggttccaa ctttcaccat aatgaaataa gatcactacc gggcgtattt tttgagttat      780
cgagattttc aggagctaag gaagctaaaa tgagccatat tcaacgggaa acgtcttgct      840
cgaggccgcg attaaattcc aacatggatg ctgatttata tgggtataaa tgggctcgcg      900
ataatgtcgg gcaatcaggt gcgacaatct atcgattgta tgggaagccc gatgcgccag      960
agttgtttct gaaacatggc aaaggtagcg ttgccaatga tgttacagat gagatggtca     1020
ggctaaactg gctgacggaa tttatgcctc ttccgaccat caagcatttt atccgtactc     1080
ctgatgatgc atggttactc accactgcga tcccagggaa aacagcattc caggtattag     1140
aagaatatcc tgattcaggt gaaaatattg ttgatgcgct ggcagtgttc ctgcgccggt     1200
tgcattcgat tcctgtttgt aattgtcctt ttaacggcga tcgcgtattt cgtctcgctc     1260
aggcgcaatc acgaatgaat aacggtttgg ttggtgcgag tgattttgat gacgagcgta     1320
atggctggcc tgttgaacaa gtctggaaag aaatgcataa gcttttgcca ttctcaccgg     1380
attcagtcgt cactcatggt gatttctcac ttgataacct tattttttgac gaggggaaat     1440 taataggttg tattgatgtt ggacgagtcg gaatcgcaga ccgataccag gatcttgcca     1500
tcctatggaa ctgcctcggt gagttttctc cttcattaca gaaacggctt tttcaaaaat     1560
atggtattga taatcctgat atgaataaat tgcagtttca cttgatgctc gatgagtttt     1620
tctgagggcc caaatgtaat cacctggctc accttcgggt gggcctttct gcgttgctgg     1680 cgttttttcca taggctccgc cccccctgacg agcatcacaa aaatcgatgc tcaagtcaga     1740
ggtggcgaaa cccgacagga ctataaagat accaggcgtt tccccctgga agctccctcg     1800
tgcgctctcc tgttccgacc ctgccgctta ccggatacct gtccgccttt ctcccttcgg     1860
gaagcgtggc gctttctcat agctcacgct gtaggtatct cagttcggtg taggtcgttc     1920
gctccaagct gggctgtgtg cacgaacccc cgttcagccc gaccgctgc gccttatccg     1980 gtaactatcg tcttgagtcc aacccggtaa gacacgactt atcgccactg gcagcagcca     2040
ctggtaacag gattagcaga gcgaggtatg taggcggtgc tacagagttc ttgaagtggt     2100
ggcctaacta cggctacact agaagaacag tatttggtat ctgcgctctg ctgaagccag     2160
ttacctcgga aaaagagttg gtagctcttg atccggcaaa caaaccaccg ctggtagcgg     2220 tggtttttttt gtttgcaagc agcagattac gcgcagaaaa aaaggatctc aagaagatcc     2280 tttgatttttc taccgaagaa aggcccaccc gtgaaggtga gccagtgagt tgattgcagt     2340
ccagttacgc tggagtctga ggctcgtcct gaatgatatc aagcttgaat tcgtt          2395
```